US007738945B2

(12) United States Patent
Fauver et al.

(10) Patent No.: US 7,738,945 B2
(45) Date of Patent: Jun. 15, 2010

(54) METHOD AND APPARATUS FOR PSEUDO-PROJECTION FORMATION FOR OPTICAL TOMOGRAPHY

(75) Inventors: Mark E. Fauver, Seattle, WA (US); J. Richard Rahn, Sammamish, WA (US); Eric J. Seibel, Seattle, WA (US); Alan C. Nelson, Gig Harbor, WA (US)

(73) Assignees: University of Washington, Seattle, WA (US); VisionGate, Inc., Gig Harbor, WA (US)

(*) Notice: Subject to any disclaimer, the term of this patent is extended or adjusted under 35 U.S.C. 154(b) by 1974 days.

(21) Appl. No.: 10/716,744

(22) Filed: Nov. 18, 2003

(65) Prior Publication Data

US 2004/0076319 A1   Apr. 22, 2004

Related U.S. Application Data

(63) Continuation-in-part of application No. 10/126,026, filed on Apr. 19, 2002, now Pat. No. 7,197,355.

(51) Int. Cl.
*A61B 5/05* (2006.01)
(52) U.S. Cl. .................. 600/425; 356/444; 382/133
(58) Field of Classification Search .............. 356/444; 382/133; 600/425
See application file for complete search history.

(56) References Cited

U.S. PATENT DOCUMENTS

| 3,470,373 A | 9/1969 | Brewer |
| 3,497,690 A | 2/1970 | Wheeless, Jr. |
| 3,598,471 A | 8/1971 | Baldwin |
| 3,657,537 A | 4/1972 | Wheeless, Jr. |
| 3,748,468 A | 7/1973 | Hartman |

(Continued)

FOREIGN PATENT DOCUMENTS

JP   02085747 A   3/1990

(Continued)

OTHER PUBLICATIONS

Kikuchi, S. et al., "Three-dimensional computed tomography for optical microscopes," Optics Communications 107 (1994) 432-444.

(Continued)

*Primary Examiner*—Long V Le
*Assistant Examiner*—Ellsworth Weatherby
(74) *Attorney, Agent, or Firm*—Citadel Patent Law; George A. Leone

(57) ABSTRACT

A system for optical imaging of a thick specimen that permits rapid acquisition of data necessary for tomographic reconstruction of the three-dimensional (3D) image. One method involves the scanning of the focal plane of an imaging system and integrating the range of focal planes onto a detector. The focal plane of an optical imaging system is scanned along the axis perpendicular to said plane through the thickness of a specimen during a single detector exposure. Secondly, methods for reducing light scatter when using illumination point sources are presented. Both approaches yield shadowgrams. This process is repeated from multiple perspectives, either in series using a single illumination/detection subsystem, or in parallel using several illumination/detection subsystems. A set of pseudo-projections is generated, which are input to a three dimensional tomographic image reconstruction algorithm.

24 Claims, 18 Drawing Sheets

U.S. PATENT DOCUMENTS

| | | | |
|---|---|---|---|
| 3,833,762 A | 9/1974 | Gudmundsen | |
| 3,960,449 A | 6/1976 | Carleton | |
| 3,999,047 A | 12/1976 | Green | |
| 4,175,860 A | 11/1979 | Bacus | |
| 4,200,353 A | 4/1980 | Hoffman | |
| 4,293,221 A | 10/1981 | Kay | |
| 4,360,885 A * | 11/1982 | Edgar | 382/131 |
| 4,873,653 A | 10/1989 | Grosskopf | |
| 4,891,829 A | 1/1990 | Deckman et al. | |
| 5,141,609 A | 8/1992 | Sweedler et al. | |
| 5,148,502 A * | 9/1992 | Tsujiuchi et al. | 382/255 |
| 5,281,517 A | 1/1994 | Bacus et al. | |
| 5,308,990 A | 5/1994 | Takahashi et al. | |
| 5,312,535 A | 5/1994 | Waska et al. | |
| 5,321,501 A | 6/1994 | Swanson et al. | |
| 5,402,460 A | 3/1995 | Johnson | |
| 5,428,447 A | 6/1995 | Toida | |
| 5,547,849 A * | 8/1996 | Baer et al. | 435/7.24 |
| 5,548,395 A | 8/1996 | Kosaka | |
| 5,552,605 A | 9/1996 | Arata | |
| 5,668,887 A | 9/1997 | Parker et al. | |
| 5,673,300 A | 9/1997 | Reckwerdt | |
| 5,680,484 A * | 10/1997 | Ohyama et al. | 382/255 |
| 5,710,429 A | 1/1998 | Alfano et al. | |
| 5,741,411 A | 4/1998 | Yeung et al. | |
| 5,760,901 A | 6/1998 | Hill | |
| 5,760,951 A | 6/1998 | Dixon et al. | |
| 5,828,408 A | 10/1998 | Mottin et al. | |
| 5,848,123 A | 12/1998 | Strommer | |
| 5,878,103 A | 3/1999 | Sauer et al. | |
| 5,880,838 A | 3/1999 | Marx et al. | |
| 5,909,476 A * | 6/1999 | Cheng et al. | 378/4 |
| 5,915,048 A | 6/1999 | Hill et al. | |
| 5,987,158 A | 11/1999 | Meyer | |
| 6,005,617 A | 12/1999 | Shimamoto et al. | |
| 6,026,174 A * | 2/2000 | Palcic et al. | 382/133 |
| 6,037,579 A | 3/2000 | Chan et al. | |
| 6,038,067 A | 3/2000 | George | |
| 6,047,080 A | 4/2000 | Chen et al. | |
| 6,072,624 A | 6/2000 | Dixon et al. | |
| 6,078,681 A | 6/2000 | Silver | |
| 6,091,983 A | 7/2000 | Alfano et al. | |
| 6,130,958 A | 10/2000 | Rohler et al. | |
| 6,165,734 A | 12/2000 | Garini | |
| 6,192,144 B1 | 2/2001 | Holz | |
| 6,201,628 B1 | 3/2001 | Basiji | |
| 6,211,955 B1 | 4/2001 | Basiji | |
| 6,215,587 B1 | 4/2001 | Alfano et al. | |
| 6,248,988 B1* | 6/2001 | Krantz | 250/201.3 |
| 6,249,341 B1 | 6/2001 | Basiji | |
| 6,251,586 B1 | 6/2001 | Mulshine | |
| 6,251,615 B1 | 6/2001 | Oberhardt | |
| 6,252,979 B1 | 6/2001 | Lee | |
| 6,312,914 B1* | 11/2001 | Kardos et al. | 435/6 |
| 6,388,809 B1 | 5/2002 | MacAulay | |
| 6,452,179 B1 | 9/2002 | Coates et al. | |
| 6,519,355 B2 | 2/2003 | Nelson | |
| 6,522,775 B2 | 2/2003 | Nelson | |
| 6,529,614 B1 | 3/2003 | Chao et al. | |
| 6,591,003 B2 | 7/2003 | Chu | |
| 6,636,623 B2 | 10/2003 | Nelson | |
| 6,640,014 B1* | 10/2003 | Price et al. | 382/255 |
| 6,775,399 B1 | 8/2004 | Jiang | |
| 6,868,177 B1 | 3/2005 | Camahort | |
| 2001/0012069 A1 | 8/2001 | Derndinger et al. | |
| 2001/0040094 A1* | 11/2001 | Inaba et al. | 204/603 |
| 2002/0161534 A1 | 10/2002 | Adler et al. | |
| 2003/0049841 A1* | 3/2003 | Short et al. | 435/449 |
| 2003/0118223 A1 | 6/2003 | Rahn | |
| 2003/0137669 A1* | 7/2003 | Rollins et al. | 356/479 |
| 2003/0210760 A1 | 11/2003 | Nelson | |
| 2003/0210814 A1 | 11/2003 | Nelson | |
| 2003/0222197 A1 | 12/2003 | Reese | |
| 2004/0001618 A1 | 1/2004 | Johnson | |
| 2004/0008515 A1 | 1/2004 | Brown | |
| 2004/0228520 A1 | 11/2004 | Dresser | |

FOREIGN PATENT DOCUMENTS

| | | |
|---|---|---|
| JP | 10260131 A | 9/1998 |
| JP | 2000121550 A | 4/2000 |
| WO | WO0111341 A2 | 2/2002 |
| WO | WO0218537 A2 | 3/2002 |
| WO | WO0235474 A1 | 5/2002 |
| WO | WO 02/095476 A2 | 11/2002 |

OTHER PUBLICATIONS

Kikuchi, S. et al., "Three-dimensional microscopic computed tomography based on general Radon transform for optical imaging systems," Optics Communications 123 (1996).

Matula, P. et al. "Precise 3D image alignment in micro-axial tomography," Journal of Microscopy, vol. 209, Pt. 2 (Feb. 2003) pp. 126-142.

Ong, SH, Development of an imaging flow cytometer. Anal Quant Cytol Histol 9(5)pp. 375-382, 1987.

Gilbert, P, "Iterative Methods for the Three dimensional Reconstruction of an Object from Projections," Journal of Theoretical Biology 36pp. 105-117, 1972.

Oppenheim, BE, More Accurate Algorithms for Iterative 3 dimensional Reconstruction, IEEE Transactions on Nuclear Science NS-21pp. 72-77, 1974.

Singer, JR, Grunbaum, FA, Kohn, P, and Zubelli, JP, "Image Reconstruction of the Interior of Bodies that Diffuse Radiation," Science 248(4958)pp. 990-993, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237, 2001.

Bellman, SH, Bender, R, Gordon, R, and Rowe, JE, "Art is Science being A Defense of Algebraic Reconstruction Techniques for Three dimensional Electron Microscopy," Journal of Theoretical Biology 32pp. 205-216. 1971.

Manglos, SH, Jaszcak, RJ, and Floyd, CE, "Maximum Likelihood Reconstruction for Cone Beam SPECT: Development and Initial Tests,". Physics in Medicine and Biology 34(12)pp. 1947-1957,1989, #1382.

Manglos, SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241, 1995, #4389.

Hampel, U and Freyer, R, "Fast Image Reconstruction for Optical Absorption Tomography in Media with Radially Symmetric Boundaries", Medical Physics 25 (1)pp. 92-101, 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2)pp. 183-193.1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, 3$^{rd}$ ed., Wiley-Liss, 1995.

HJ Tiziani and MI Uhde, Three-dimensional analysis by a microlens array confocal arrangements (*Applied Optics* 33, 567 [1994]).

Bayat, S, Le Duc, G, Porra, L, Berrruyer, G, Nemoz, C, Monfraix, S, Fiedler, S, Thomlinson, W, Suortti, P, Standertskjold-Nordenstam, CG, and Sovijarvi, Ara, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Kinney, JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197, 1988.

Kinney, JH and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," Science, vol. 296, pp. 541-545, Apr. 19, 2002.

Sharpe, J, review, "Optical Projection Tomography as a New Tool for Studying Embryo Anatomy," *J. Anat.* (2003), pp. 175-181.

RH Anderson, "Close-up imaging of documents and displays with lens arrays," *Applied Optics* 18, 477 (1979).

Kak, A.C. and Slaney, M., *Principles of Computerized Tomographic Imaging*, IEEE Press, New York, 1988.

E.G. Steward, *Fourier Optics: An Introduction*, 2nd ed. (Halsted Press, New York, 1987).

A. Klug and J.L. Finch, "Structure of viruses of the papilloma-polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Banda-Gamboa et al., "Spectral-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements," Cytometry, vol. 2, No. 5, pp. 327-336 (1982).

M. Rozycka, et al., "Optical Diffraction as a Tool for Semiautomatic, Quantitative Analysis of Tissue Specimens," Cytometry, vol. 2, No. 4, pp. 244-248 (1982).

Almeida and Fuji, Fourier transform differences and averaged simularities in diatoms, Applied Optics, vol. 18, No. 10, pp. 1663-1667, (1979).

Smolinska and Dawidowicz, "Extraction of common or different part from optical images," Institute of Physics, Warsaw Technical University, 222-223.

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149-156, 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Ostrowski, et al., "Application of Optical Diffractometry in Studies of Cell Fine Structure," Histochemistry (1983) 78:435-449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18-24 (1986).

Bem, W, et al., "Modification of Chromatin Pattern in the Course of Terminal Differentiation During Human Granulocytopiesis: Optical Diffractometry Study," Cellular and Molecular Biology 33(5), 563-571 (1987).

Rozycka, M, et al., "Analysis of chromatin pattern in blood lymphocytes of healthy donors and in lymphoid cells of patients with chronic lymphocytic leukaemia," J. Clin. Pathol. 1988:41:504-509.

George, JS et al., "Virtual Pinhole Confocal Microscope," Physics Division Progress Report, www.lanl.gov/p/pdfs/papp_pinhole.pdf, (1999-2000).

Pawley, JB, *Handbook of Biological Confocal Microscopy*, Plenum Press, NY, 479-490 (1995).

* cited by examiner

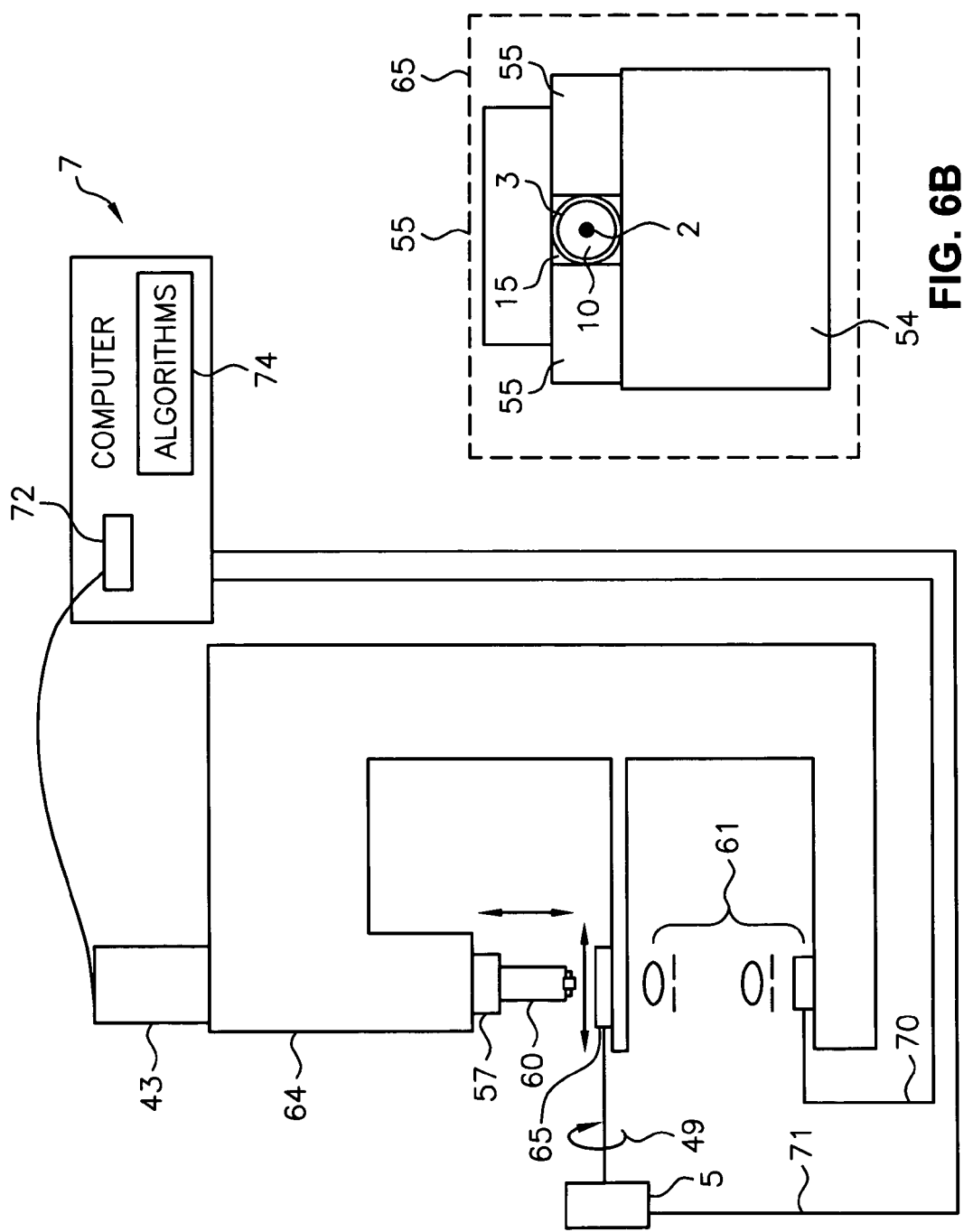

METHOD AND APPARATUS FOR PSEUDO-PROJECTION FORMATION FOR OPTICAL TOMOGRAPHY

RELATED APPLICATIONS

This application is a continuation-in-part (CIP) of co-pending U.S. patent application Ser. No. 10/126,026, filed Apr. 19, 2002, of Nelson entitled "Variable Motion Optical Tomography of Small Objects," which is incorporated herein by this reference.

FIELD OF THE INVENTION

The present invention is related to optical systems and, more particularly, to optical systems for extended depth-of-field imaging through a thick specimen (i.e. non-planar) to generate shadowgrams, wherein the apparatus permits the rapid acquisition of data necessary for tomographically reconstructing the three dimensional (3D) image of a specimen useful in applications such as high-resolution optical tomography of micron-scale objects.

BACKGROUND OF THE INVENTION

Overview

For some imaging applications, it is desirable to generate information in three dimensions within a thick specimen. An optical tomographic device is intended to produce three-dimensional reconstructions of specimens by providing a multitude of 'shadowgrams', a shadowgram (a.k.a. projection) being a measure of light attenuation along a set of ray paths through the specimen. An ideal shadowgram contains only information about absorption of the specimen, and has an infinite depth-of-field, with no change in spatial frequency response along the axis of projection. Computed tomographic algorithms such as filtered backprojection, are used to convert the set of shadowgrams into a three-dimensional volume image.

The approach described above is effective for x-ray tomography, in which the photon wavelength is much smaller than the desired spatial resolution. However, in high-resolution optical tomography, the illumination photon wavelength(s) may be on the order of the desired spatial resolution and object feature size, a projection image obtained in a manner analogous to the methods of x-ray tomography will be obscured due to diffraction of the incident light by the specimen features. Thus, means for rejecting or reducing the effects of scattered light must be employed to obtain a useful shadowgram. It is critical in computational tomographic image reconstruction that the photon path from source, through the object and onto the array detector is known geometrically and that only photons along the single line path reach a single-detector element. Because photons are scattered or deflected from their straight-line paths, particularly in passing through the object, the detector elements may receive photons from unknown locations within the object. Such scattering can become a significant problem when the scattered photon intensity in any given detector element exceeds that of the signal-to-noise limit in the reconstruction process. Therefore, it is desirable to remove the scattered (non-ballistic) photons from the detected image. In addition, refraction must also be controlled to preserve the ideal straight ray paths from illumination source to detector.

The methods for controlling or rejecting scattered light can be divided into two functional categories: point-source-based projection and pseudoprojection. Point source based projection methods employ an illumination point source and detector in an analogous manner to that used for X-ray tomography. Shadowgram quality is improved (mainly by controlling or reducing scattered light) by minimizing the source-object-detector distance, by using virtual sources, by using wavelength-shifting cell-bound probes, by limiting the acceptance angle of the detector array, by polarization, by reducing wavelength, or by confocal-like rejection. Pseudoprojection methods employ imaging optics to provide a shadowgram such that the depth of field is at least as large as the region of interest of the specimen. One method for accomplishing this is through use of long depth-of-field imaging optics, preferably with a long working distance to accommodate as many source-detector pairs as possible, such that the large number of views obtained increases the three-dimensional reconstructed image resolution compared with the resolution of a single shadowgram. Another method involves extending the depth of field by mechanically scanning the focal plane in a continuous manner, and integrating the images onto a detector. This method provides better spatial frequency response along the optical axis (better 3D MTF) compared with using long depth-of-field imaging optics because of the greater rejection of out-of-focus light by a high-NA objective.

Shadowgram Formation

The latter pseudoprojection method is the one of primary interest in this patent. To obtain a three-dimensional representation of an object, a microscope objective is axially scanned such that its plane of focus scans through the specimen's thickness. The focal plane of the objective lens can be moved through the specimen while the detector is located in the microscope's image plane. Thus, a projection image can be compiled from a set of discrete focal planes within the specimen.

Some example descriptions of discrete focal-plane scanning are provided by N Ohyama et al., in U.S. Pat. No. 5,680,484 issued Oct. 21, 1997, entitled "Optical Image Reconstructing Apparatus Capable of Reconstructing Optical Three-Dimensional Image Having Excellent Resolution and S/N Ratio"; by E A Swanson et al., in U.S. Pat. No. 5,321,501 issued Jun. 14, 1994, entitled "Method and Apparatus for Optical Imaging with Means for Controlling the Longitudinal Range of the Sample"; by R E Grosskopf, in U.S. Pat. No. 4,873,653 issued Oct. 10, 1989, entitled "Microscope System for Providing Three Dimensional Resolution"; and by A D Edgar, in U.S. Pat. No. 4,360,885 issued Nov. 23, 1982, entitled "Micro-Optical Tomography." However, all these methods suffer from low throughput rates due to the stopping and restarting of the moving parts. Furthermore, the spacing between each focal plane places a limit on the spatial resolution that can be achieved, and storage of the separate images requires large amounts of computer memory. Since each pixel is measured only once, no reconstruction is done. These methods simply assemble discrete focal-plane scans into a 3D image with additional sampling errors from reconstructing from a set of projections. In addition, out-of-focus light from the other focal planes contributes to undesirable spurious signals (blurring) in the assembled image. The blurring can be reduced by using an objective lens with a short depth of field or by using confocal microscopy.

In contrast to the drawbacks of the background art, the present invention provides a method and apparatus for continuously scanning the focal plane of an optical imaging system along an axis perpendicular to said plane through the thickness of a specimen during a single detector exposure. This then generates a shadowgram (projection image), whose resolution can depend on the depth of focus of the moving focal plane, as well as on the lateral spatial resolution (i.e., the resolution within the focal plane). The light that exits the specimen region should therefore comprise a shadowgram of the specimen as seen from an individual perspective as viewed from a particular angle of rotation. The process is repeated from multiple perspectives, either in series using a single illumination/detection subsystem, or in parallel using several illumination/detection subsystems, or some combination of series and parallel acquisition. In this way, a set of pseudo-projections is generated, which can be input to a tomographic image reconstruction algorithm (such as filtered backprojection) to generate a three-dimensional image. The apparatus described has greater speed and higher signal-to-noise than the prior art described above while providing a means for 3D reconstruction by computer-aided tomographic techniques. The method disclosed may be useful in applications such as high-resolution optical tomography of small objects.

Application to Cell Imaging

In application, high resolution optical tomography is of primary interest for three-dimensional imaging cells and cell nuclei; these specimens are the primary motivation for imaging on the micron scale. The invention is described herein with respect to specific examples relating to biological cells; however, it will be understood that these examples are for the purpose of illustrating the principals of the invention, and that the invention is not so limited. In one example, constructing a three-dimensional distribution of point densities and emission intensities within a microscopic volume allows the measurement of density and fluorescence at any location within the microscopic volume and determines the location of structures, molecules or molecular probes of interest. By using tagged molecular probes, the quantity of probes that attach to specific structures in the microscopic object may be measured. For illustrative purposes, an object such as a biological cell may be labeled with at least one tagged molecular probe, and the measured amount and location of this probe may yield important information about the disease state of the cell, including, but not limited to, various cancers such as lung, colon, prostate, breast, cervical and ovarian cancers, or infectious agents.

Sample preparation has also been problematic for prior methods. For example, others have had problems with simple vacuum-based insertion of cells or relying on capillary action to wick-up the cell suspension. The present invention has overcome such drawbacks. Methods for using cells in micro-capillary tubes for optical tomography are also presented herein.

Image Reconstruction

After acquiring a series of two-dimensional projections (shadowgrams), image reconstruction is used to create the three dimensional image. The most common and easily implemented reconstruction algorithms, known as filtered backprojection methods, are derived from a similar algorithm in x-ray computed tomography (CT) using parallel-beam geometry. (See the following references, for example, Kak, A. C. and Slaney, M., *Principles of Computerized Tomographic Imaging*, IEEE Press, New York, 1988, and Herman, G., *Image Reconstruction from Projections: The Fundamentals of Computerized Tomography*, Academic Press, New York, 1980). These methods are based on theorems for Radon transforms with modifications that reflect the particular geometry of the source/detector configuration and the ray paths in the irradiating beam.

SUMMARY OF THE INVENTION

In the current invention, a variety of methods for generating optical shadowgrams for use in optical CT are presented. One such method is accomplished by moving an objective lens, thereby scanning the focal plane through the thickness of the specimen region, such that the entire specimen thickness is scanned continuously during a single detector exposure interval. The procedure is repeated from several perspectives over an arc of up to 180 degrees, using one or more pairs of light sources and detector arrays simultaneously. The specimen can be rotated and/or translated to acquire additional shadowgram viewpoints. The methods of (CT) image reconstruction can then be applied to obtain a high-quality three-dimensional reconstruction of the specimen region. Other methods presented herein involve reducing scattered light when generating a shadowgram using illumination point source-based projection.

BRIEF DESCRIPTION OF THE DRAWINGS

FIG. 6A and FIG. 6B illustrate schematically one embodiment of the present invention, incorporating a microscope objective lens mounted on a piezoelectric translation device.

DETAILED DESCRIPTION OF THE PREFERRED EMBODIMENTS

General Embodiments

Figure 1:
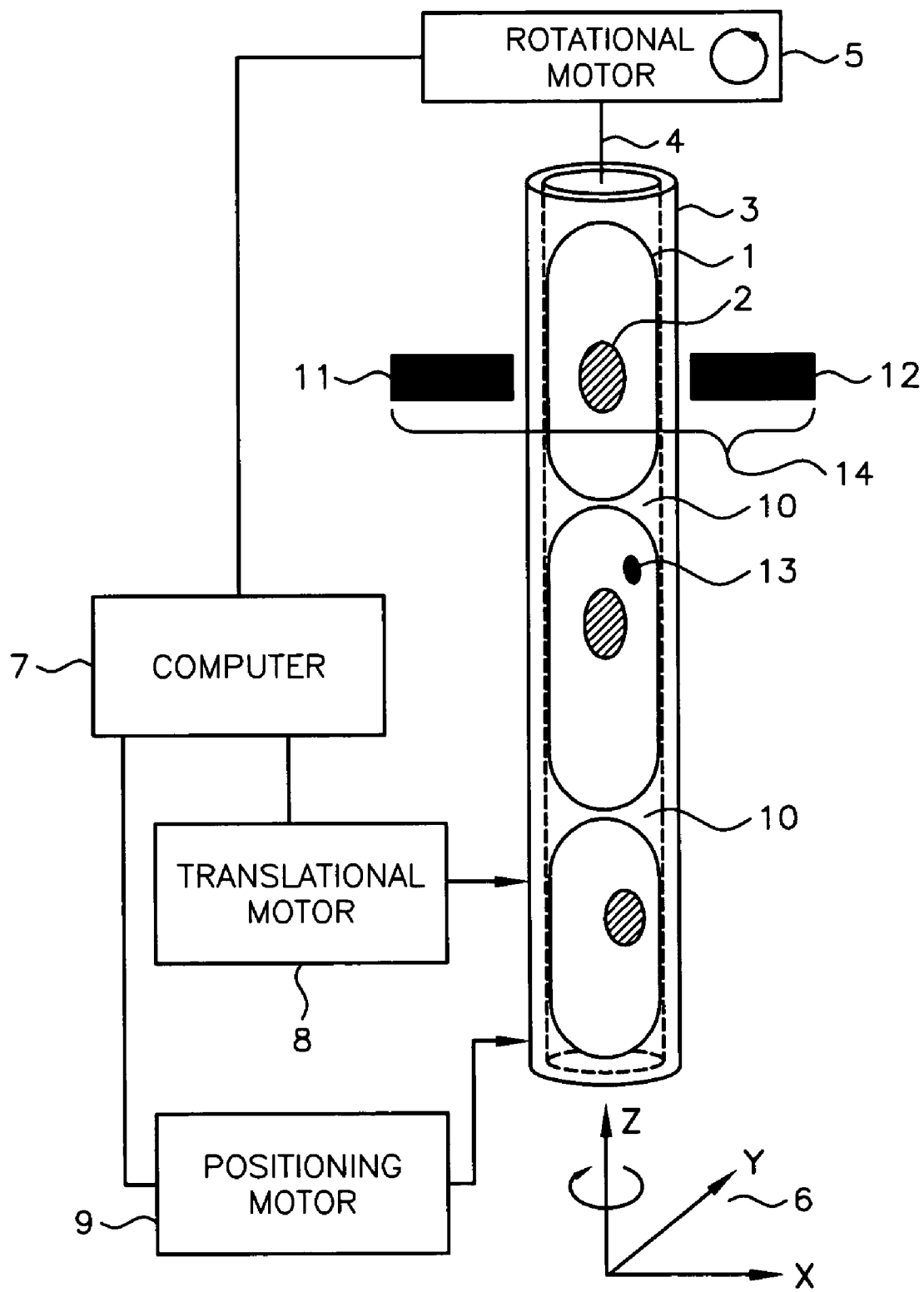
FIG. 1 schematically shows an example illustration of cells packed into a capillary tube as contemplated by an embodiment of the present invention.

Referring now to FIG. 1, there shown schematically is an example illustration of cells packed into a capillary tube as contemplated by an embodiment of the present invention. In this example embodiment, a section of the capillary tube 3 is filled with cells 1 that are packed rigidly into the tube. Each of the cells may include a nucleus 2. The capillary tube 3 has a central axis 4 oriented with reference to a coordinate system 6 having coordinates in the x, y and z-directions. In some instances, at least one molecular probe 13 may be bound within the cell. A computer 7 is coupled to provide control signals to a rotational motor 5 and a translational motor 8. It will be recognized that equivalent arrangements of one or more motors, gears or fluidics or other means of generating motion may also be employed to achieve the necessary translational and rotational motion of the capillary tube or other substrate. In some cases, one or more of the motors may be replaced by manual positioning devices or gears or by other means of generating motion such as hydraulic or piezoelectric transducers. The axis of translation is the z-axis, and rotation is around the z-axis. The positioning motor 9 is coupled to move the cell in a plane defined by the x, y-axes, substantially perpendicular to the central axis for the purpose of centration, as necessary.

It will be recognized that the curved surface of the capillary tube will act as a cylindrical lens and that this focusing effect may not be desirable in a projection system. Those skilled in the art will appreciate that the bending of photons by the tube can be eliminated if the spaces between (a) the illumination source 11 and the tube and (b) between the tube surface and the detector 12 are filled with a material 10 whose index of refraction matches that of the capillary tube and that the tube can be optically coupled (with oil or a gel, for example) to the space filling material. When index of refraction differences are necessary, for instance due to material choices, then at minimum the index of refraction difference should only exist between flat surfaces in the optical path. Illumination source 11 and detector 12 form a source-detector pair 14. Note that one or more source-detector pairs may be employed.

Consider the present example of cells packed into a capillary tube. The cells may preferably be packed single file so that they do not overlap. The density of packing whole cells of about 100 microns in diameter into a capillary tube with diameter less than 100 microns can be roughly 100 cells per centimeter of tube length. For bare nuclei of about 20 microns in diameter, the packing can be roughly 500 nuclei per centimeter of tube length where the tube diameter is proportional to the object size, about 20 microns in this case. Thus, within several centimeters of capillary tube length, a few thousand non-overlapping bare nuclei can be packed. By translating the tube along its central axis 4, motion in the z-direction can be achieved. In an alternative arrangement, the cells can flow within the tube. Moving the tube in the x, y-directions allows objects within the tube to be centered, as necessary, in the reconstruction cylinder of the optical tomography system. By rotating the tube around its central axis 4, a multiplicity of radial projection views can be produced. Moving the tube in the z-direction with constant velocity and no rotation simulates the special case of flow optical tomography.

One advantage of moving a tube filled with cells that are otherwise stationary inside the tube is that objects of interest can be stopped, then rotated, at speeds that permit nearly optimal exposure for optical tomography on a cell-by-cell basis. That is, the signal to noise ratio of the projection images can be improved to produce better images than may be usually produced at constant speeds and direction typical of flow systems. Objects that are not of interest can be moved out of the imaging system swiftly, so as to gain overall speed in analyzing cells of interest in a sample consisting of a multitude of cells. Additionally, the ability to stop on an object of interest, and then rotate as needed for multiple projections, nearly eliminates motion artifacts. Still further, the motion system can be guided at submicron movements and can advantageously be applied in a manner that allows sampling of the cell at a resolution finer than that afforded by the pixel size of the detector. More particularly, the Nyquist sampling criterion could be achieved by moving the system in increments that fill half a pixel width, for example. Similarly, the motion system can compensate for the imperfect fill factor of the detector, such as may be the case if a charge-coupled device with interline-transfer architecture is used.

In another embodiment, the capillary tube 3 may be replaced with a solid medium in a cylindrical shape, and having cells embedded within. This solid medium comprises a polymer or UV-cure polymer, or cell mounting medium formed into a cylindrical shape, creating an optically clear cylinder, like that of a polymer optical fiber, with cells embedded. The embedding may be accomplished by extruding a liquid suspension or by other means.

Figure 2:
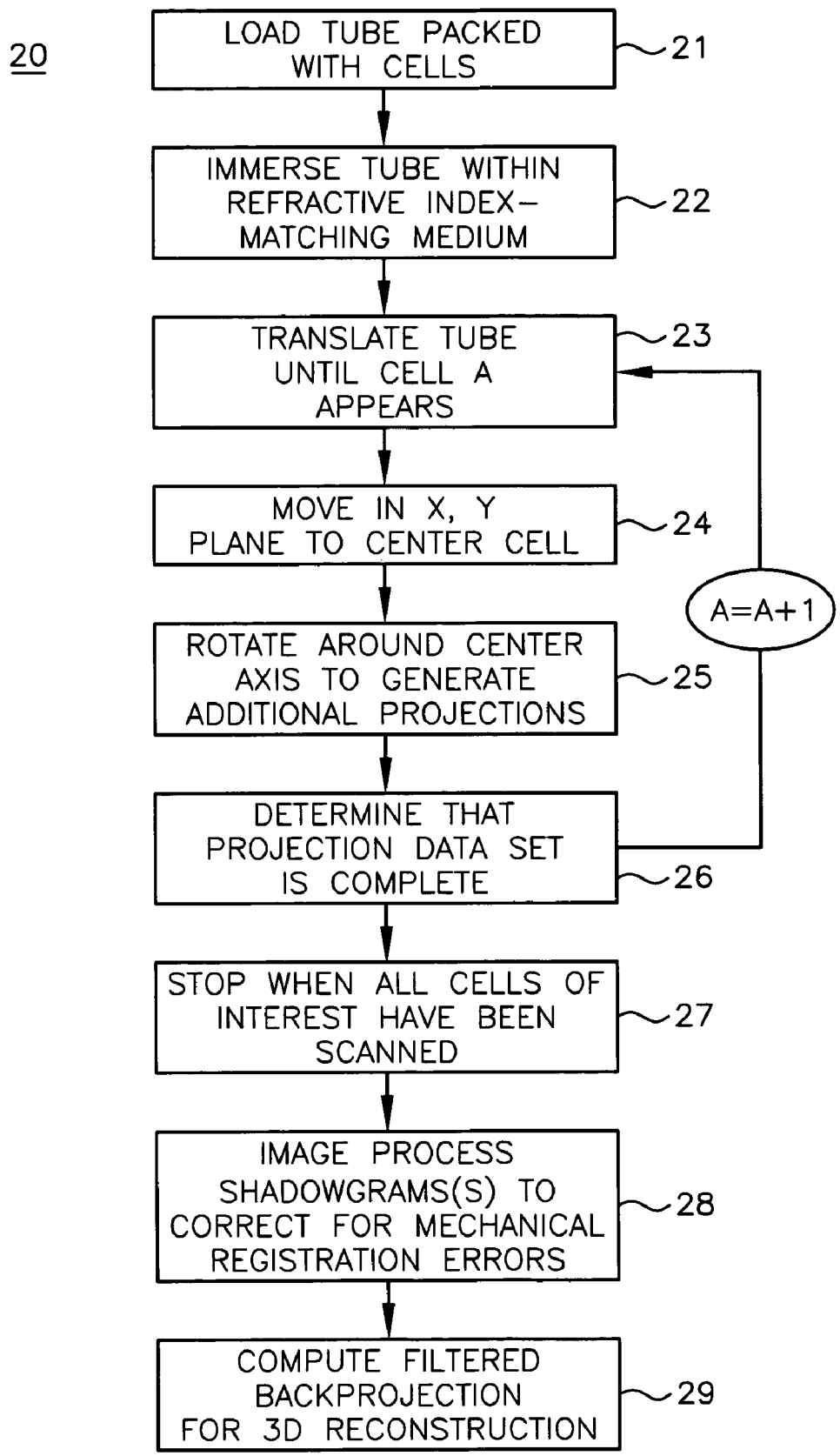
FIG. 2 schematically shows an example of a flow diagram illustrating the steps prior to the three-dimensional (3D) image reconstruction as contemplated by an embodiment of the present invention.

Referring now to FIG. 2, an example of a flow diagram illustrating the three-dimensional (3D) image acquisition as contemplated by an embodiment of the present invention is shown. As contemplated by one example of the present invention, a 3D imaging process 20 includes the steps of loading the tube packed with cells at step 21, immersing the tube within a refractive index-matched medium 22, translating the tube until the first cell of interest has been located at step 23, centering the cell of interest, as necessary, at step 24, generating a set of projections at each different rotation angle at step 25, determining when the data set is complete at step 26, and repeating the process from steps 23 through 26 until all cells of interest have been analyzed. The process of acquiring shadowgrams stops at step 27. The process may be implemented in a computer software program executed by a personal computer such as computer 7, for example. During and/or after image acquisition, images may be corrected for mechanical registration errors at step 28, and image reconstruction performed to obtain the three-dimensional image at step 29.

Figure 3A:
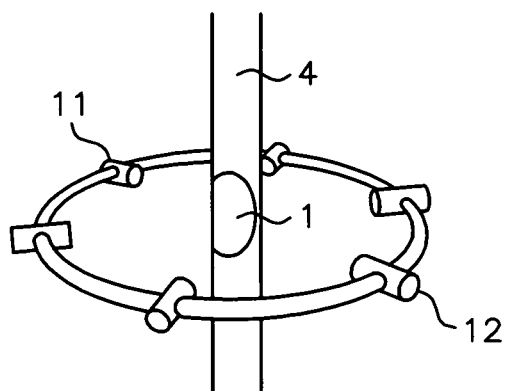
FIGS. 3A, 3B 3C, 3D, 3E and 3F schematically show the types of arrangements of source-detector pairs in an optical tomography system as single plane, and multiple planes.
Figure 3B:
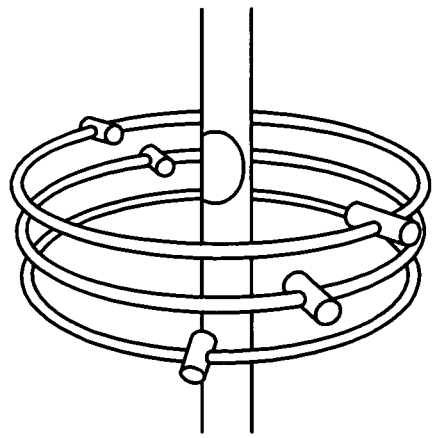
Figure 3C:
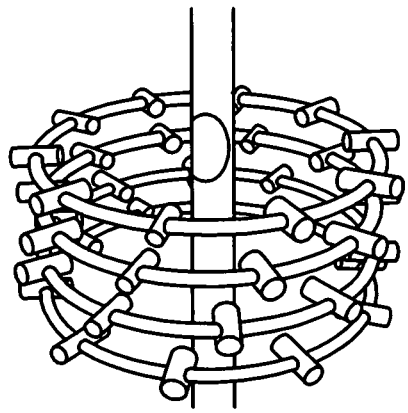
Figure 3D:
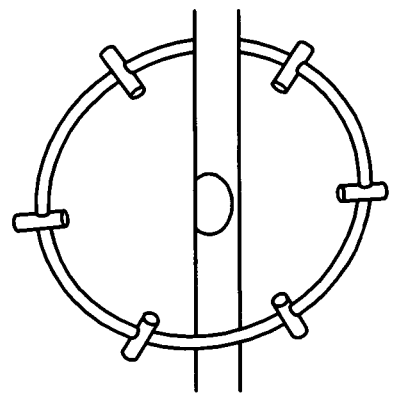
Figure 3E:
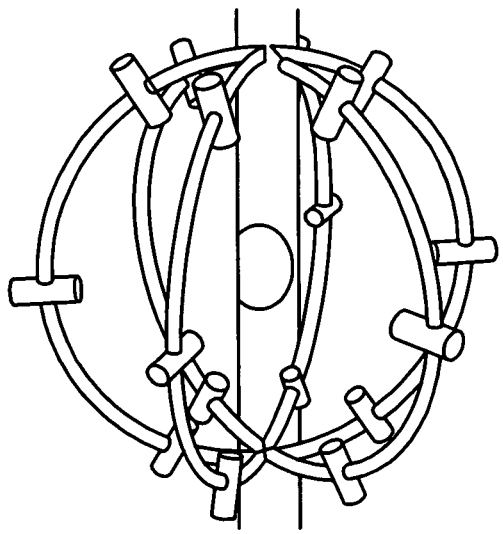
Figure 3F:
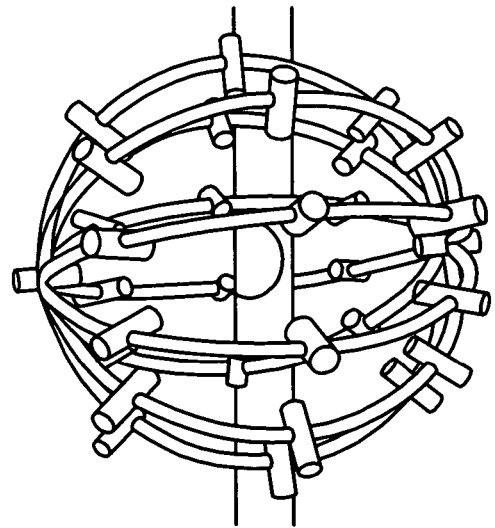

Referring now to FIGS. 3A, 3B 3C, 3D, 3E and 3F, there shown are some example types of geometries possible for illumination sources 11 and detectors 12. Note that the rings are shown only to illustrate the planar configuration within the sources and detectors lie, and do not necessarily represent a physical structure. In all configurations, the tube may be rotated and/or translated to provide an adequate number of views for three-dimensional reconstruction. FIG. 3A is an example of one or more source-detector pairs 14 arranged in a plane, said plane being orthogonal to the axis 4 of the tube. FIG. 3B is an example of one source-detector pair per plane, employing multiple parallel planes. All planes are orthogonal to tube axis 4, with an angular offset between consecutive planes. The specimen, such as cell 1, is translated along the tube axis, and single shadowgrams are acquired in serial fashion. FIG. 3C shows source-detector pairs arranged in a plane parallel to the tube axis 4. The multitude of source-detector pairs in each plane allows acquisition of multiple shadowgrams simultaneously (in parallel fashion). As the cell is translated from one source-detector plane to the next, an angular offset provides new views. Typically, a decrease in shadowgram resolution occurs by increasing the distance between source and detector, but increases the number of projections acquired simultaneously. This increase in parallelism of shadowgram acquisition improves overall throughput of the device. Acquiring more (angular) views increases voxel resolution in the three-dimensional reconstruction. FIG. 3D shows the source-detector pairs oriented in a plane parallel to the tube axis. FIG. 3E and FIG. 3F show the possibility of orienting source-detector pairs in multiple planes, with the set of planes forming a common point of intersection. The degree of parallelism of shadowgram acquisition can be increased by using illumination source-detector array pairs that lie in multiple planes, each with a common intersection point. This parallelism increases speed of acquisition and reduces the possibility for registration errors because the specimen moves less, or not at all, between shadowgram acquisitions. While translation and/or rotation of the specimen in the tube may be performed, ideally all viewpoints necessary for three-dimensional reconstruction would be performed simultaneously to obtain maximum sample throughput. FIG. 3E illustrates a geometry that is favorable for rotation of the specimen to acquire more views.

Figure 4A:
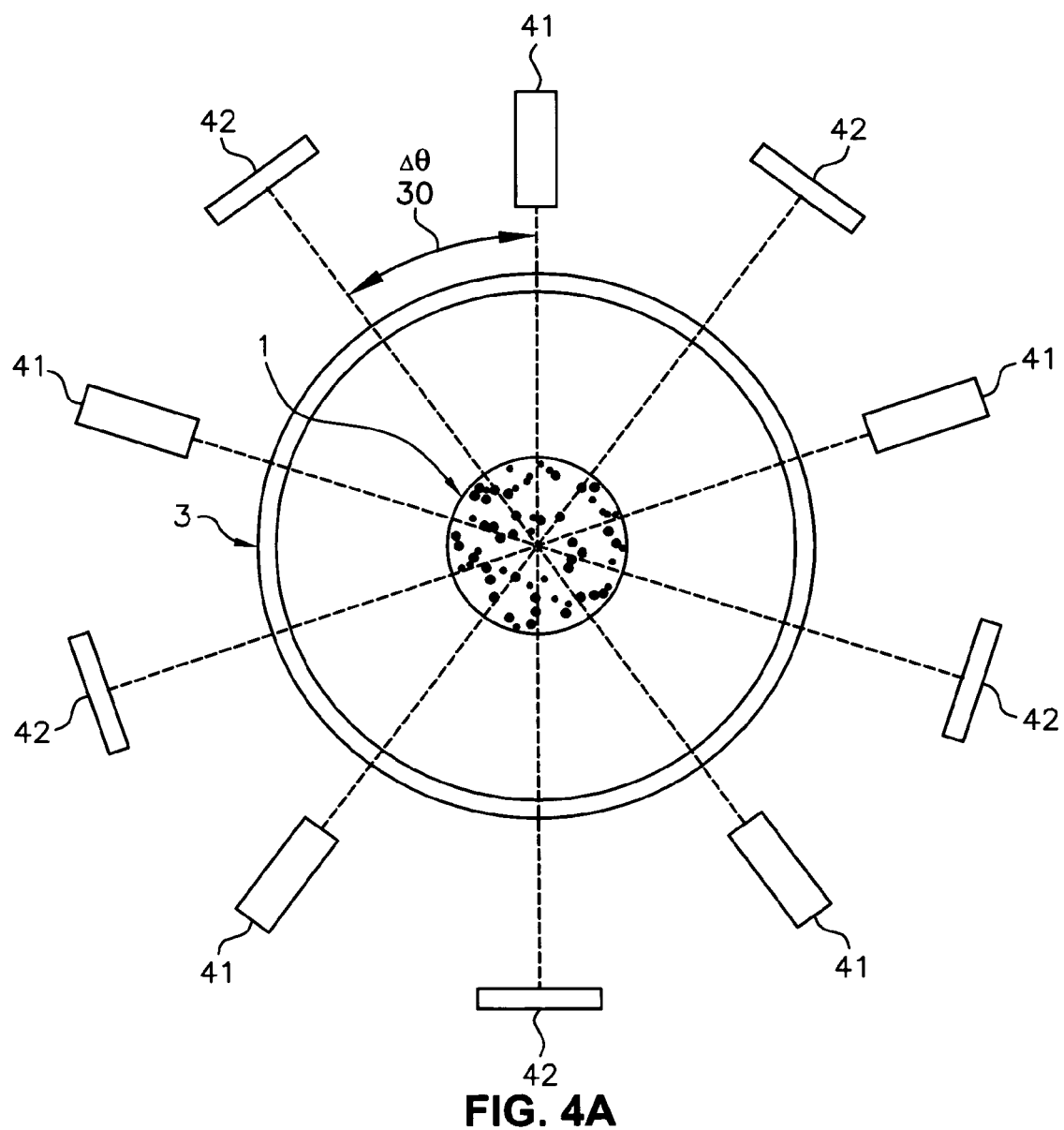
FIG. 4A illustrates an example of an optical tomography system employing multiple sets of pseudo-projection viewing subsystems about a single specimen, as contemplated by one embodiment of the present invention.
Figure 4B:
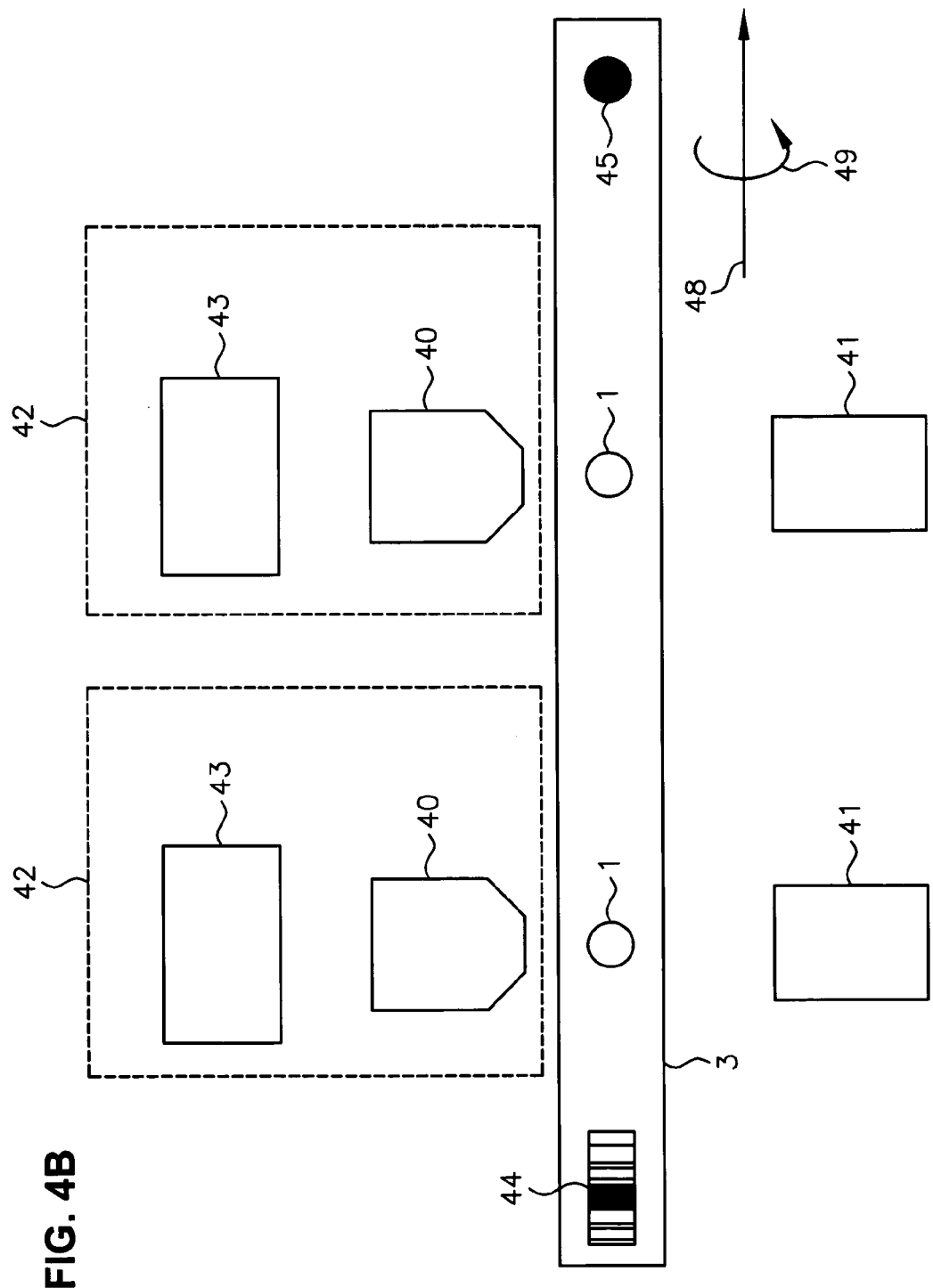
FIG. 4B illustrates an example of an optical tomography system employing multiple sets of pseudoprojection viewing subsystems along a series of different specimens as contemplated by an alternate embodiment of the invention.

Referring now to FIG. 4A and FIG. 4B an example of an optical tomography system employing multiple sets of source-detector pairs, as contemplated by the present invention is schematically shown. In FIG. 4A, multiple perspectives are captured in parallel from the same specimen, using two or more optical imaging systems, each comprising, as a minimum, a light source, a PZT, an objective, and a detector array. There shown is a specimen, such as a cell 1 or a nucleus 2, within a medium having a predetermined index of refraction captured in a micro-capillary tube 3. A detector system 42 each includes an objective micro-lens 40 and CCD or CMOS camera 43 juxtaposed to receive light from an illumination system 41 including a light source, condenser lens, and one or two apertures as commonly used in condenser assemblies (separate components not shown). The detector system 42 may be seen as a more specific embodiment of the detector 12, and the illumination system 41 as a more specific embodiment of illumination source 11. It will be understood that each of the two or more optical imaging systems may incorporate additional or alternative components, such as those described in the other embodiments as, for example, an epi-illumination system which adds a beam splitter but reduces the number of lenses by the capillary by half. The two or more optical imaging systems are arranged about the central axis of the micro-capillary tube at regular intervals; the number of systems used being limited by the desired numerical aperture (NA) to be captured by each imaging system and geometric constraints.

As an illustrative example, consider five such imaging systems, as depicted in FIG. 4A. In this example, a detector system 42 of each imaging system is separated by a predetermined angular increment $\Delta\theta$ 30, from a corresponding illumination portion 41 of the adjacent imaging system. In the example embodiment $\Delta\theta$ is 36 degrees. This arrangement permits each objective lens to accommodate a higher NA than would be possible if the light-capturing portions 42 were adjacent to one another; in this example, an NA approaching 0.59 (=sin [½×360/5]) is possible.

A projection image exhibits a two-fold rotational symmetry; thus a perspective acquired from angle $\theta>180°$ is equal to the projection image acquired from angle $\theta-180°$. Therefore, the direction of the light path form source to detector may be flipped by 180° without affecting the resulting projection image. The configuration depicted in FIG. 4A exploits this fact to obtain more efficient arrangement of the sources and detectors. The scanning positions of the n light-capturing portions 42 can be run in phase, if desired, such that all of them are moving toward the center of the specimen such as cell 1 at the same time. In this way, the overall system's center of mass remains stationary, making it easier to reduce mechanical vibrations and undesired mechanical stresses.

In the example method depicted in FIG. 4A, the angular increment $\Delta\theta$ remains the same while the total angle of rotation, $\theta_{tot}$ is equal to 180/n−$\Delta\theta$. In the present example, n=5, and thus an angular rotation of (36−$\Delta\theta$) degrees is required, instead of the (180−$\Delta\theta$) degrees that would be necessary if only a single source and detector were in use. Table 1 shows the order in which the angles may be acquired, using an example angular increment $\Delta\theta$=2 degrees. In the first data acquisition time interval, perspectives are acquired for $\theta$=0, 36, 72, 108, and 144 degrees from the five imaging systems 42, the tube is then rotated by $\Delta\theta$=2 degrees, and perspectives are then acquired for $\theta$=2, 38, 74, 110, and 146 degrees. These steps are repeated until perspectives are acquired for $\theta$=34, 70, 106, 142, and 178 degrees; data for all the necessary perspectives have now been collected.

In another method, which may also be employed using the configuration depicted in FIG. 4A, the angular increment $\Delta\theta$ is equal to 10 degrees. With this angular increment, the perspectives are acquired in 2-degree increments over 18 time intervals.

TABLE 1

| Step No. | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| | | | | | | | | Angle of Acquired Projection | | | | | | | | | | | |
| Imaging | | 0 | 0 | 2 | 4 | 6 | 8 | 10 | 12 | 14 | 16 | 18 | 20 | 22 | 24 | 26 | 28 | 30 | 32 | 34 |
| System | 216 | 36 | 38 | 40 | 42 | 44 | 46 | 48 | 50 | 52 | 54 | 56 | 58 | 60 | 62 | 64 | 66 | 68 | 70 |
| Angle | 72 | 72 | 74 | 76 | 78 | 80 | 82 | 84 | 86 | 88 | 90 | 92 | 94 | 96 | 98 | 100 | 102 | 104 | 106 |
| | 288 | 108 | 110 | 112 | 114 | 116 | 118 | 120 | 122 | 124 | 126 | 128 | 130 | 132 | 134 | 136 | 138 | 140 | 142 |
| | 144 | 144 | 146 | 148 | 150 | 152 | 154 | 156 | 158 | 160 | 162 | 164 | 166 | 168 | 170 | 172 | 174 | 176 | 178 |

TABLE 2

| Step No. | | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| | | | | | | | | Angle of Acquired Projection | | | | | | | | | | | |
| Imaging | | 0 | 0 | 10 | 20 | 30 | 40 | 50 | 60 | 70 | 80 | 90 | 100 | 110 | 120 | 130 | 140 | 150 | 160 | 170 |
| System | 216 | 36 | 46 | 56 | 66 | 76 | 86 | 96 | 106 | 116 | 126 | 136 | 146 | 156 | 166 | 176 | 6 | 16 | 26 |
| Angle | 72 | 72 | 82 | 92 | 102 | 112 | 122 | 132 | 142 | 152 | 162 | 172 | 2 | 12 | 22 | 32 | 42 | 52 | 62 |
| | 288 | 108 | 118 | 128 | 138 | 148 | 158 | 168 | 178 | 8 | 18 | 28 | 38 | 48 | 58 | 68 | 78 | 88 | 98 |
| | 144 | 144 | 154 | 164 | 174 | 4 | 14 | 24 | 34 | 44 | 54 | 64 | 74 | 84 | 94 | 104 | 114 | 124 | 134 |

In the present example, the configuration that corresponds to Table 1 is expected to be faster, since the total angle of rotation is smaller ($\theta_{tot}$=34 degrees) than the configuration associated with Table 2 ($\theta_{tot}$=170 degrees). The time savings will be larger if the acceleration and deceleration times are not negligible. Thus a preferred method of data collection, according to this embodiment, is the one corresponding to Table 1. However, it is understood that other configurations, including but not limited to the one associated with Table 2, are included in this invention. Following the acquisition of one or more projection exposures from a single perspective, the specimen is rotated as best shown in FIG. 4A or rotated and/or translated as shown, for example in FIG. 4B, by a small angle about an axis that is, typically, perpendicular to the PZT's direction of motion. Once this rotation ceases, another series of one or more projection exposures is acquired from this new perspective; and the specimen is then rotated further. This process may continue until the total change in angle from the first perspective has reached up to 180 degrees. A three-dimensional reconstruction of the specimen can then be generated from the accumulated data.

Referring now particularly to FIG. 4B, an example of an optical tomography system employing multiple sets of source-detector pairs along a series of different specimens as contemplated by an alternate embodiment of the invention is schematically illustrated. A plurality of specimens such as cells 1 or nuclei 2 may be carried by a rigid medium having one or more fiducials 45 for registration. Each of the multiple sets of pseudo-projection viewing subsystems include an image detector 42 such as a CCD or CMOS camera, disposed to receive image information from an objective lens 40, illuminated by an illumination system 41 comprised of a illumination source, condenser lens, and two apertures. The rigid medium may comprise a micro-capillary tube 3 or a polymer optical fiber, or other equivalent media, for example. Specimen samples are moved through various stations of source-detector pairs along the direction indicated by arrow 48. Each fiducial 45, such as an opaque microsphere, aids in detecting specimen positioning and positional shifts during translation and/or rotation, and may be used with conventional automatic image registration techniques on the images being integrated on the image detector, or on individual images that are being summed for a single integration by the computer. The registration of the multiple projections is corrected as the rigid medium is rotated as indicated by arrow 49. In contrast to prior art techniques, the present invention moves the objective lens with respect to the specimen to scan the focal plane continuously and sums the images optically at the detector, and is not restricted to summing individual images acquired and summed only electronically. Unique indicia 44, such as a micro-barcode, may be placed to identify and to maintain a chain of custody for each of the plurality of specimens.

Figure 5A:
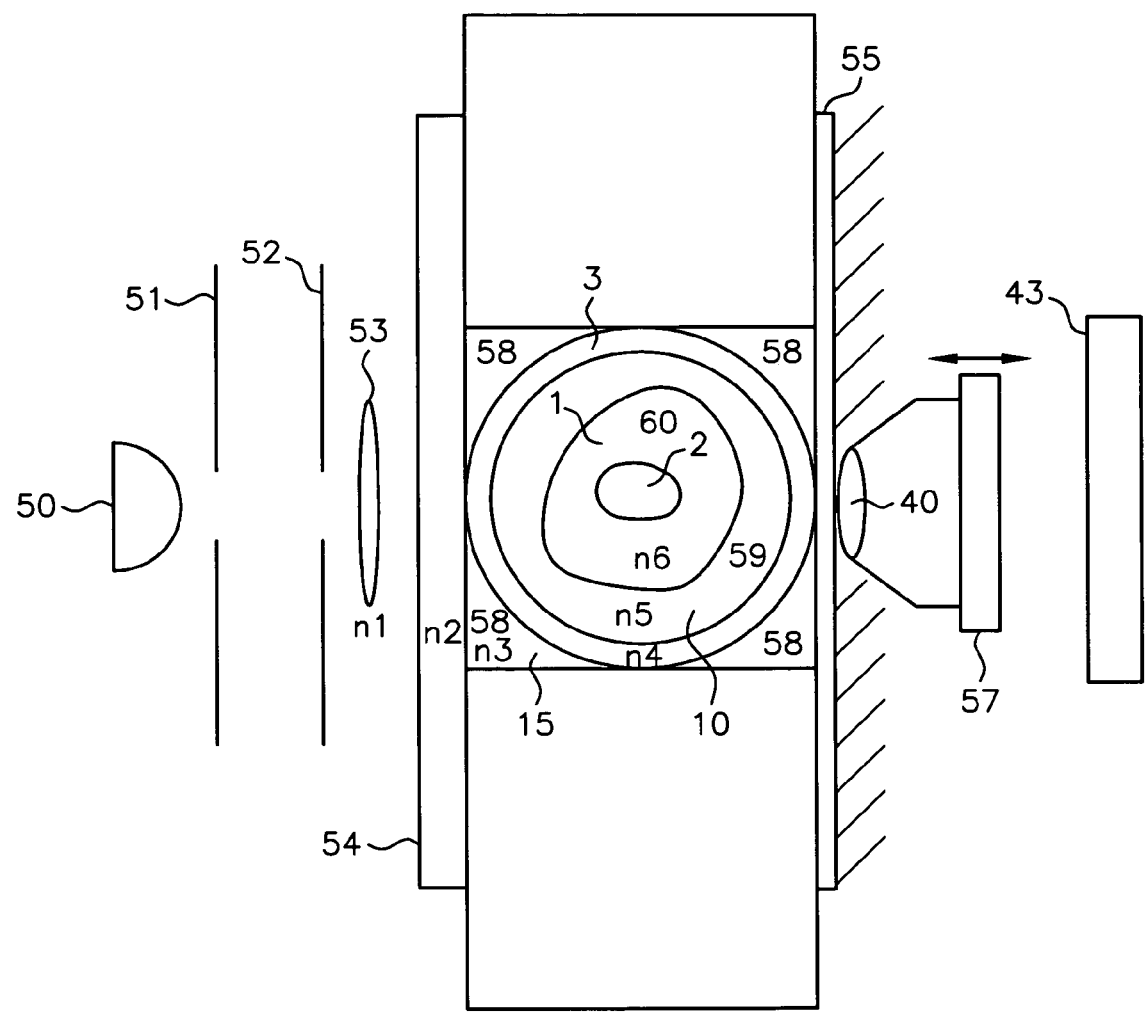
FIG. 5A schematically shows a cell within a micro-capillary tube that can be rotated for taking multiple projections and an objective lens that can be axially scanned using pseudo-projection techniques.

Referring now to FIG. 5A, there shown is a close-up view of a single specimen, as for example a single cell, immersed within a medium of optical indexing material. The single specimen is shown within a micro-capillary tube 3 (e.g. one such tube is manufactured by Polymicro Technologies, LLC., AZ, US) that can be rotated for taking multiple projections and an objective lens 40 that can be axially scanned is schematically shown. An illumination source includes a light source 50 that projects light through an aperture 51, a stop 52, and through a condenser lens 53 that is positioned before a microscope slide 54. A micro-capillary tube 3 holds a cell 1 between the slide and a thin coverslip 55. An objective lens 40, preferably an oil-immersion lens, is disposed to receive light passed through the micro-capillary tube 3. The objective lens is translated along the optical axis by an actuator 57 such as a piezoelectric element. The coverslip 55 must be thin enough so that the distance between the center of the micro-capillary tube and the outer surface of the coverslip is smaller than the working distance of the objective lens. The condenser lens 53 is within the index of refraction $n_1$ (e.g. air). The slide 54 and coverslip 55 have index of refraction $n_2$. A region 58 surrounding the micro-capillary tube 3 contains index-matching medium 15 such as optical gel or immersion oil, which has index of refraction $n_3$. The micro-capillary tube 3 itself has index of refraction $n_4$. The region 59 surrounding the cell 1 within the micro-capillary tube contains a medium 10 possessing an index of refraction $n_5$. A region 60 within the cell may be filled with the same medium 10, or may differ in its index of refraction $n_6$. It is preferred that $n_3=n_4=n_5=n_6$ (differences must be minimized) between the two flat parallel surfaces formed by slide 54 and coverslip 55 to avoid a cylindrical lens distortion. The image is projected onto a camera 43.

In another embodiment, a micro-objective lens, solid immersion lens, or microlens array is used instead of a microscope objective 40. This enables the scan speed to increase due to the reduction in weight. In yet another embodiment, the condenser assembly (50,51,52,53) is replaced with an illumination point source, and objective lens 40 and actuator 57 may be removed, such that this embodiment is not restricted to pseudoprojection, but also includes point source-based projection.

Figure 5B:
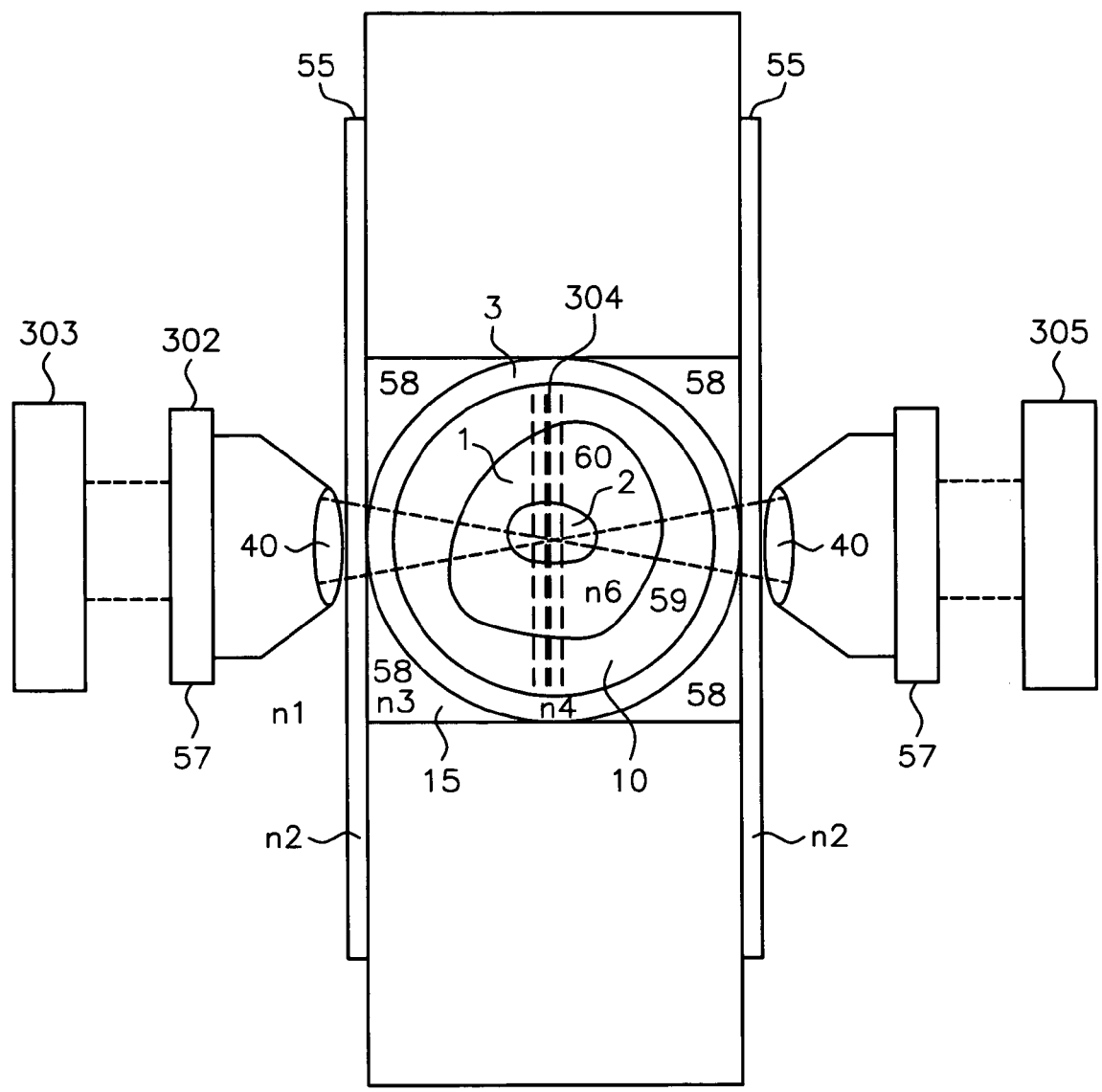
FIG. 5B schematically shows a cell within a micro-capillary tube that can be rotated for taking multiple slices of two-dimensional images using confocal scanning techniques.

Referring now to FIG. 5B, in yet another embodiment, a matching objective lens system 302, including a pair of objective lenses 40, and actuators 57 symmetrically placed on both sides of the cell 1 within a micro-capillary tube 3, for the purpose of using a confocal scanning technique in transmission is shown. One of the objective lenses 40 is illuminated to function as an illuminating lens and the second serves as a collecting objective lens. Due to the symmetrical nature of the apparatus and the use of imaging a single cell that can be centered within the capillary tube due to Poiseuille laminar flow (parabolic laminar flow), the optical path length is well controlled between objective lenses. Very small optical path differences between rays from one objective lens 40 to the other will allow the use of confocal imaging in transmission without loss of contrast and resolution as compared to confocal microscopes imaging thicker specimens with uncontrolled optical path differences. The total optical path difference is defined as the net sum of the index of refraction multiplied by the difference in length of the optical ray along each of the total ray paths.

Some examples of confocal scanning beam optical imaging or mapping systems for macroscopic samples are disclosed in U.S. Pat. Nos. 5,760,951 issued Jun. 2, 1998, and 6,072,624 to Dixon et al., issued Jun. 6, 2000, in which an expanded laser beam passes through a scan system and a telecentric laser scan lens focuses the beam to a moving spot in the sample. In addition, a virtual pinhole technique was disclosed by J. S. George in U.S. Pat. No. 6,038,067 issued Mar. 14, 2000, that alleviates the problem of maintaining an array of pinholes (spatial light filters) aligned during confocal scanning in either the transmission or reflection modes. U.S. Pat. Nos. 5,760,951, 6,038,067 and 6,072,624 are all incorporated herein in their entirety by reference. Light reflected (or emitted) from the illuminated spot is collected by the laser scan lens, descanned by the scan system, and detected by a confocal detector. In one embodiment an array of point sources (e.g. created by a pinhole array, a spatial light modulator, or microlens array) are used to create an array of light beams for illuminating a specimen. A pixel-array detector, such as a camera, with virtual pinhole image post processing by computer software is made conjugate to the array of point sources. The array of point sources can be scanned directly or their resultant optical beams can be scanned as an array of illumination beams by one or more mirrors 303, while the descanning requirement is eliminated by having an array of confocal detectors with virtual pinhole filters of the collected light signals. In this case descanning mirrors 305 are replaced by the array of confocal detectors.

In the present invention, a plurality of two-dimensional image slices of the object of interest may be obtained by scanning both the illuminating light beams by one or two scanning mirrors 303 and the collecting light beams by one or two descanning mirrors 305 in synchrony so that the confocal arrangement stays in optical alignment. Since the objective lenses are typically larger in size, the two-dimensional image slice is scanned faster by having the illuminating beam of light be scanned by one or two mirrors before reaching the objective lens. Thus, after the collection lens the transmitted beam of light containing the signal will be scanned in the opposite manner (i.e. descanned) to insure confocality of the scanned and transmitted beam.

A three-dimensional image is assembled by capturing a series of these two-dimensional image slices along the optical axis that is perpendicular to the dotted vertical lines 304. A new image slice can be generated by changing the plane of focus of the two objective lenses in synchrony, stepping the axial position of the two objective lens assemblies with respect to the capillary tube, or adjusting the capillary tube position along the optical axis. The capillary tube can be rotated to generate a second three-dimensional view of the cell, which is used to compensate for the non-symmetric point spread function of the objective lens, producing lower axial resolution than lateral resolution.

A system having one pinhole at the illumination side and a conjugate pinhole at the collection side of a specimen in transmission confocality can be expanded by having a one-dimensional or two-dimensional array of pinholes, microlenses, or spatial light modulators (e.g. liquid crystal or micromirror array) thus increasing the speed of imaging and decreasing the scan range of the scanning and descanning mirrors or objective lenses. The detector for the scanned beams in parallel can be a camera instead of a single pixel fast detector such as a photomultiplier tube. The descanning mirrors are not necessary if the camera is made optically conjugate to the array of micro-light sources or pinhole apertures in transmission. By post processing the camera images (e.g. where the camera is a CCD device) so that only the central point of focus is acquired and the surrounding light is eliminated, a virtual pinhole spatial filter can be created in software. This method is most useful with an array of scanning point sources that are imaged onto the video camera so that physical alignment of multiple spatial filters is not necessary to maintain.

Using Color Information

In order to discriminate between image contrast due to absorption, and image contrast due to refraction, the use of color information is important. While the range of wavelengths absorbed by the dye or marker typically occupies a narrow band and/or has a peak absorption, the range of wavelengths refracted is typically much larger, or at least differs from the absorption band of the dye/marker. The image can be separated based on color to produce two or more images, with one image primarily consisting of features generated by absorption by the dye/marker used.

For cells which have significant texturing of the cytoplasmic boundary, refractive contrast may dominate at some angles of viewing, making it more difficult to obtain information about the stained portions of the cell (i.e. nucleus). Thus separating the image by color, with one image formed from wavelengths only due to absorption of the dye/marker, or possibly limited to a narrow range of absorption by the dye/marker. The image then contains primarily features whose contrast was generated due to absorption of the dye, and at least partially eliminates feature contrast due to refractions. This provides a more ideal projection for performing optical tomographic reconstruction (three dimensional). Another image consisting of part or all of the other wavelengths (excluding those of the first image) can be generated, the primary mechanism of contrast generation being refraction. This 'refraction image' may aid in detecting texturing of the cytoplasmic or nuclear boundary to determine a cell's condition.

A second use of separation of the image based on color is to reject image contrast generated by refraction, in order to form the best possible absorption image. This helps in the quantification of absorption for densitometric studies, or to improve optical density measurements.

Separation can be achieved by either using colored illumination to match the absorption peak of the dye, or post-acquisition with a color camera and performing the color separation of the image digitally.

Choice of dye/marker can greatly alter the effectiveness of this method. Dyes/Markers with narrower absorption band (a fluorophore or quantum dot can be used, as long as the emission light is separated out also) can provide greater rejection of image features generated by refracted light. For example, when using hematoxylin stain on cell nuclei, the range of illumination wavelengths might be chosen to be 585-615 nm.

Pseudoprojection Embodiments

Referring now to FIG. 6A and FIG. 6B, one embodiment of the present invention, incorporating a microscope objective lens mounted on a piezoelectric translation device is schematically shown. A piezoelectric transducer (PZT) 57 is used to move an objective lens 60 an axial distance of about 40 microns or more. In one useful embodiment, a micro-objective positioning system provides a suitable actuator 57, which is driven up and down along the z axis of tube coordinate system 6. In this embodiment, it may be used with a high numerical aperture objective, mounted on an standard transmission microscope 64 with a video camera 43 attached and a computer-controlled light source and condenser lens assembly 61. The computer-controlled condenser and light source 50 may advantageously be a light source including one or more incandescent bulbs, an arc lamp, a laser, or a light emitting diode. Computer control signals 70 are linked to the computer-controlled condenser and light source 50 for controlling light modulation.

The output from the camera 43 is stored in a computer memory 72. A specimen assembly 65 can be translated along the x or y axes of tube coordinate system 6. In addition, a micro-capillary tube 3 containing the specimen can be rotated about its "θ" axis 49, via a rotational stage 5 that can be computer-controlled. As used herein micro-capillary tube is defined as a capillary tube having a diameter where the field of view for microscopic imaging is comparable to the capillary tube diameter. In an example embodiment the rotational stage 5 is controlled by control signals 71 as provided by the computer 7. For high speed applications other controls may be added in order to reduce vibrations during an axial scan.

Referring now particularly to FIG. 6B, the specimen assembly 65 comprises a microscope slide 54, which serves as an optically clear substrate; a micro-capillary tube 3, index matching material 15; and three coverslips 55. In one example, the micro-capillary tube 3, with inner and outer radii of approximately 50 and 150 microns respectively, contains the specimen. The micro-capillary tube 3 is placed on the slide 54 and pressed between the two coverslips 55, which are mounted to the slide 54 using an adhesive. The cover slips 55 serve to constrain the motion of the micro-capillary tube 3 along the x and y axes as defined by tube coordinate system 6. Immersing the micro-capillary tube 3 in an index matching material 15 provides lubrication during rotation about the "θ" axis 49 and provides a uniform medium between the micro-capillary tube and the coverslips 55, thus reducing optical aberrations.

The index matching material 15 is selected to allow the optical characteristics of the medium to remain substantially constant, even as the perspective presented to the objective 60 is varied. The index matching material 15 may advantageously be chosen to match the refractive index of the micro-capillary tube 3. Index matching materials are commercially available (e.g. commercial sources include Nye Optical Gels, Dymax Corp, and Cargille Labs) and include, for example optical gels, oils and fluids of varying indices of refraction for reducing light reflection at optical interfaces. Optical gels are particularly useful where higher viscosity is desired and may comprise a medium of oil, gel, polymer epoxy, or other optically transparent materials that matches refractive indices of the surroundings. Specimens can be held in index-matching epoxy, embedding media, or plastic polymer as well as index-matching gels and viscous fluids.

It should be noted that scanning focal plane methods are not limited to mechanical means. Non-mechanical means for scanning the focal plane includes the use of the chromatic aberration in lens 40 or objective lens 60 combined with shifting the center wavelength of the illumination. Non-mechanical means for scanning the focal plane also includes the use of birefringence of lenses 40 or 60 and shifting of polarization of the illumination source. Non-mechanical means for scanning the focal plane also may take advantage of spherical aberration in lenses 40 or 60 combined with annular scanning of the illumination source.

The present invention provides an improved method for sample preparation by injecting specimens within a viscous index-matched medium 15 into a micro-capillary tube using positive pressure. In one example, pressure of about 200 pounds per square inch (psi) is maintained for at least 30 minutes to accommodate the viscosity of an index matching gel. The specimen can also be stained with absorptive dyes, absorbing and light scattering dyes, antibody labels, antibodies conjugated with metal particles, quantum dots, plastic micro-spheres, fluorescent labels, and the like. Other microscopy modes may also be used, such as fluorescence, phase contrast, polarization, and dark field. A dark field mode in conjunction with a bright field mode may allow diffraction artifacts to be separated from the acquired image to improve the absorption image quality.

Figure 7:
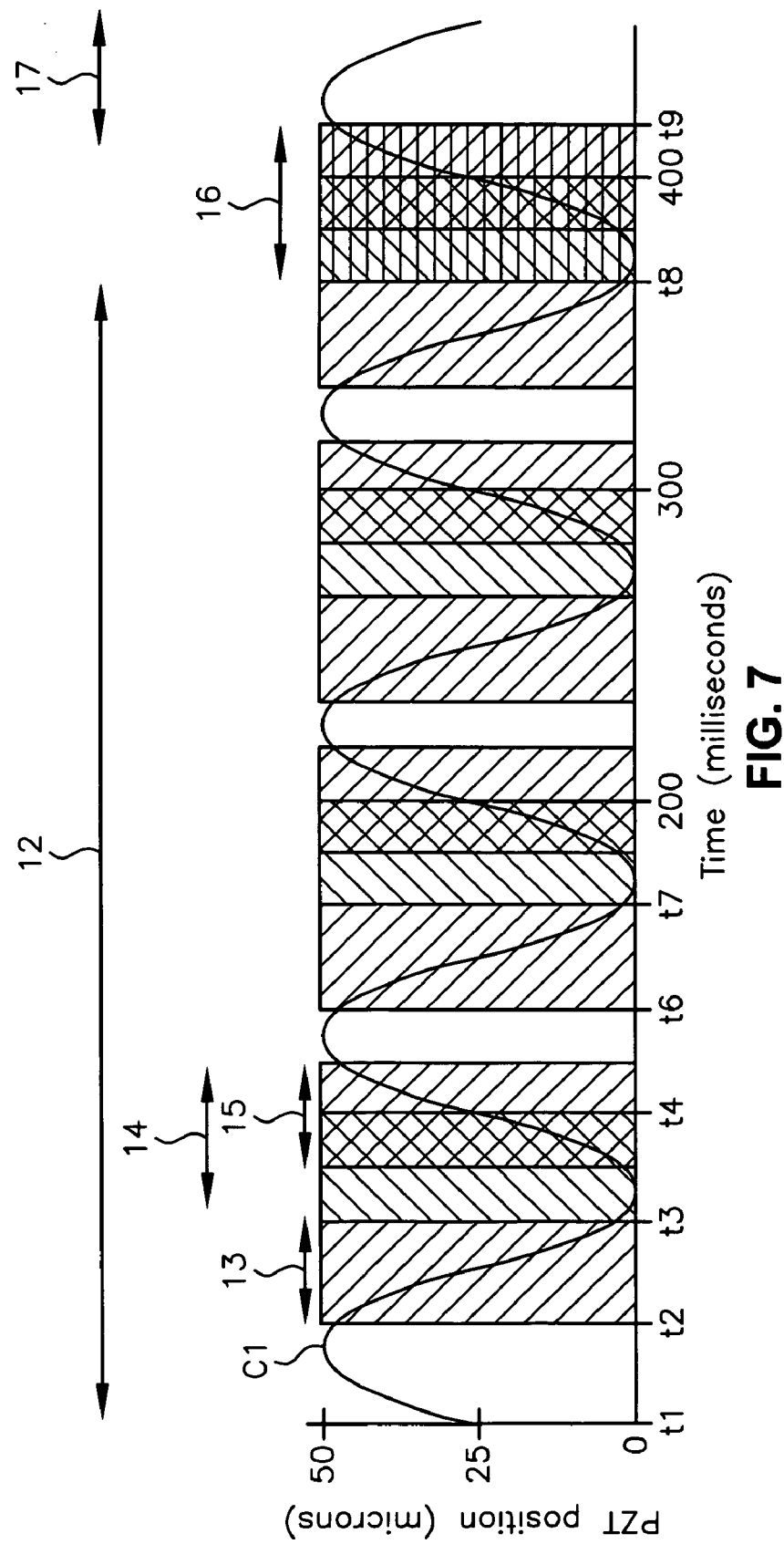
FIG. 7 depicts an example illustration of one arrangement of the timing characteristics of one embodiment of the present invention, incorporating a lens system mounted on a piezoelectric translation device.

Now referring to FIG. 7 an illustrative example of one set of possible timing characteristics for this embodiment is illustrated. The PZT-driven axial movement of the objective lens is depicted by a curve C1, which describes a sinusoidal wave with a period of 100 milliseconds (msec) and an amplitude of 25 microns. The time interval for a new perspective 12 begins at time $t_1=0$. The next stored image exposure interval I3 occurs between $t_2=33$ msec and $t_3=67$ msec. and it is saved into computer memory. It will be observed that the exposure I3 is synchronized with the objective lens movement such that the interval I3 occurs while the focal plane position is moving at a roughly constant velocity from about 25 microns above the axial center of the specimen to about 25 microns below the axial center of the specimen. A time interval for a lateral translation I4 begins immediately after the exposure interval I3, and extends until time $t_4=97$ msec. Note that there is an exposure interval I5, which overlaps in time with the lateral translation interval I4; however, because it occurs while the field of view is changing, it is not saved to computer memory. The next saved exposure interval I3 occurs between time $t_6=133$ msec and time $t_7=167$ msec. This series of operations continues until four projections, which cover the specimen's full lateral extents, have been saved to memory. The fourth saved image exposure interval I3 for this perspective I2 ends at time $t_8=367$ msec, and is followed by a rotation interval I6, an additional lateral translation interval I4, and an unsaved exposure interval I5. During the rotation interval I6, the specimen rotates about one of the lateral axes by an angle $\Delta\theta$, for example 1°. At time $t_9=417$ msec, the rotation interval I6 is complete and the time interval for a new perspective I7 begins. This procedure is repeated until up to 180/Δθ rotation intervals I6 are completed. A three-dimensional representation of the specimen can now be computed.

To increase speed and reduce multi-frame summation artifacts, a progressive scan video camera may be used instead of an interleave format. Since the specimen is scanned by relative movement of the focal plane through the specimen, alternate scanning methods include scanning the objective lens, or capillary tube, or for samples within a liquid media, scanning the specimen within capillary tube or microchannel. Mechanically scanning the objective lens (high numerical aperture) creates an extended depth of field. The condenser lens may also be scanned under Koehler illumination conditions for imaging. An infinity corrected objective is preferred to avoid magnification difference due to scanning objective but stationary camera (CCD, CMOS). The mass of objective lens may advantageously be minimized to maximize scan frequency for high speed.

In another embodiment, the system closely resembles the previous embodiment, except that the microscope system includes an aperture in the image plane to permit a confocal arrangement. In this embodiment, the depth of focus is reduced for each image plane in the integrated continuum. Doing so reduces the background level due to out-of-focus planes, which may be as large or larger than the signal level from the in focus plane. Thus a more accurate integration of the projection image can be generated when the confocal setup is used.

Because the field of view is reduced by the use of the aperture, this embodiment may also include a translational stage for moving the specimen or objective laterally in between each shadowgram. A system of rotating mirrors may also be used to scan the illumination. Each perspective will, therefore, be composed of several such shadowgrams, forming a mosaic of projections that includes the specimen's full lateral extents.

In another embodiment the system resembles the first embodiment, but the condenser lens has an aperture and field stop to alter the size and numerical aperture of the illumination. In the case where exceptionally high numerical aperture condenser is desired, the microscope slide of the assembly shown in FIG. 6B is replaced with a thin #0 coverslip (typically 130 microns thick). The condenser may be an objective lens and may include immersion materials such as index matching gels or equivalent materials.

In another embodiment, multiphoton microscopic techniques may be applied to limit depth of focus of the static imaging system (independent of movement of the objective).

In another embodiment, the specimen region may comprise an artificially generated test phantom.

In yet another embodiment, coherent monochromatic light may be used in one or multiple discrete wavelengths.

In another embodiment, other imaging modalities available for optical microscopy may be used other than bright field, such as polarization, fluorescence, phosphorescence, phase contrast, dark field, and differential interference contrast. Beamsplitters and optical filters may be required as used routinely in the field of optical microscopy.

In another embodiment, a point source such as a fiber optic core or pinhole may be used in conjunction with a lens as a condenser.

In another embodiment, the specimen and the specimen holder may be translated rather than the objective.

Figure 8A:
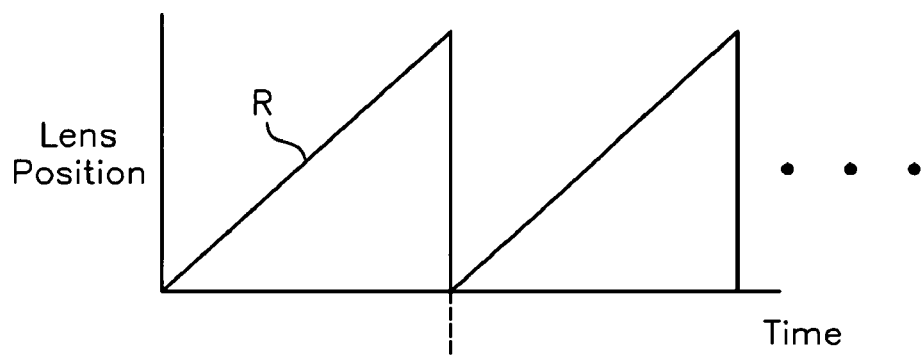
FIG. 8A and FIG. 8B show a graphical representation of specimen motion and camera exposure for a system as contemplated by the present invention.
Figure 8B:
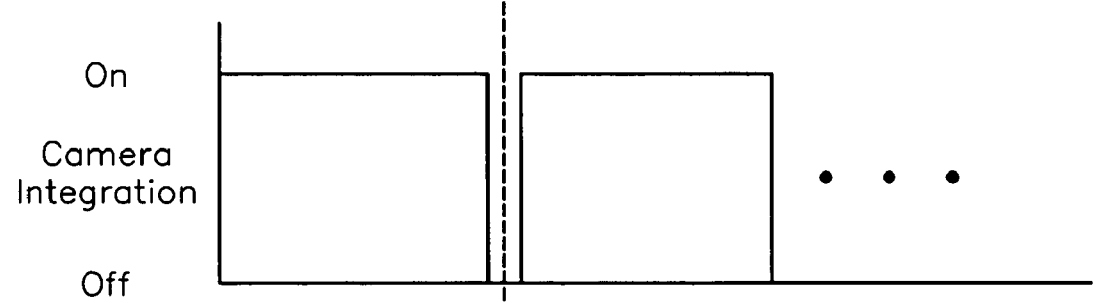

For example, as shown in FIG. 8A and FIG. 8B a graphical representation of the motion, and camera exposure for a system as contemplated by the present invention is shown. Waveform R shows a ramp function useful for driving the actuator 57 to move an objective lens 40 or 60 an axial distance of about 40 microns or more with respect to the specimen for each incremental rotation of the micro-capillary tube. This function is depicted as a linear ramp but may take the form of a sine wave, a ramp function with rounded transitions, or any other function (linear or nonlinear) to provide the desired weighting of focal plane information and the most predictable actuator motion. During a portion each period of the waveform R, the detector array is turned on for a single exposure as indicated by the "ON/OFF" function graphed in FIG. 8B. Thus, for each period of relative motion of the objective, a pseudo-projection image of the specimen is scanned onto the detector array in a continuous scan over a single exposure. Scanning is repeated for various views of the specimen as the micro-capillary tube is rotated. The pseudo-projection image thus formed is an integration of the range of focal plane images by the objective onto the detector array during each period of the scanning waveform R.

Figure 8C:
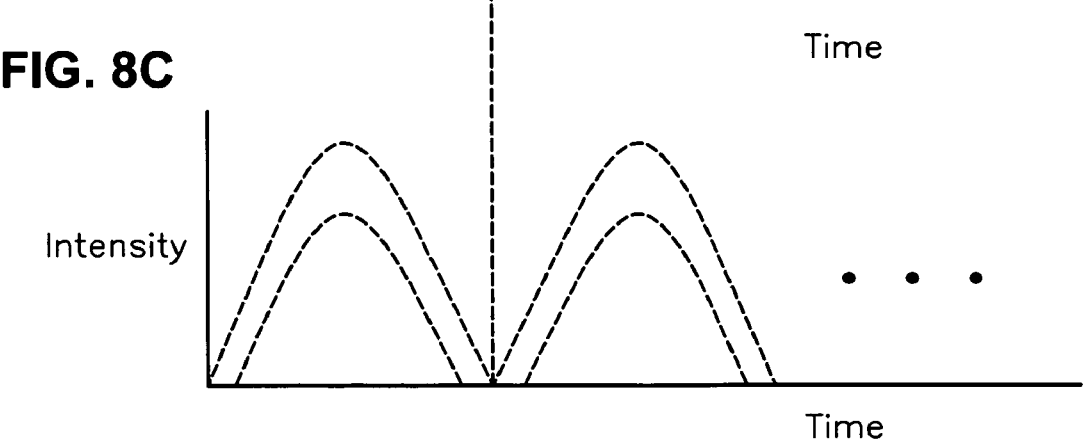
FIG. 8C graphically shows a function for scanning different focal planes in the specimen by varying the illumination intensity of the viewing subsystem as the objective is moved spatially with respect to the specimen.

Referring now to FIG. 8C, there graphically shown is a function for scanning different focal planes in the specimen by varying the illumination intensity of the viewing subsystem as the objective is moved spatially with respect to the specimen. In this case, it is not necessary to alter the integration time for the detector array to compensate for the variations in the objective's axial speed. By varying the illumination intensity with respect to focal plane position, the range of focal planes averaged by the detector array with respect to the specimen can be controlled.

Alternatively, non-linear velocity of the scanning focal plane may be employed to increase weighting from integration across areas of slower velocity and decrease the weighting of areas that are traversed more rapidly. Such differential weighting can be accomplished by varying the optical illumination levels, increasing optical illumination will increase the weighting and vice versa. For example, this may be useful for scanning the entire inner diameter of the capillary tube, however the region of interest (nucleus) may be in only one portion of the capillary of scan range of the objective lens. Therefore, the illumination may be strongest only when the focal plane is scanning the cell nuclear region. Two or more illumination sources can be applied simultaneously. For example, one is used for generation of the shadowgram, and the other source used to detect a molecular probe (i.e. fluorescent probe).

Following the acquisition of the specimen's shadowgram as seen from one perspective, the specimen may be rotated about the "θ" axis 49, and the shadowgram from a new perspective can be generated. The actuator 57 may, if desired, be driven continuously, and new images taken at a constant rate throughout the procedure; however, only those images taken at appropriate times need to be saved for inclusion in the reconstruction computation. A triggering mechanism, generated via a computer program using the actuator 57 position (or velocity) and the specimen rotation velocity as inputs, can accomplish this task. Additional embodiments may use alternative signals from the specimen or fiducials within the sample.

Figure 9:
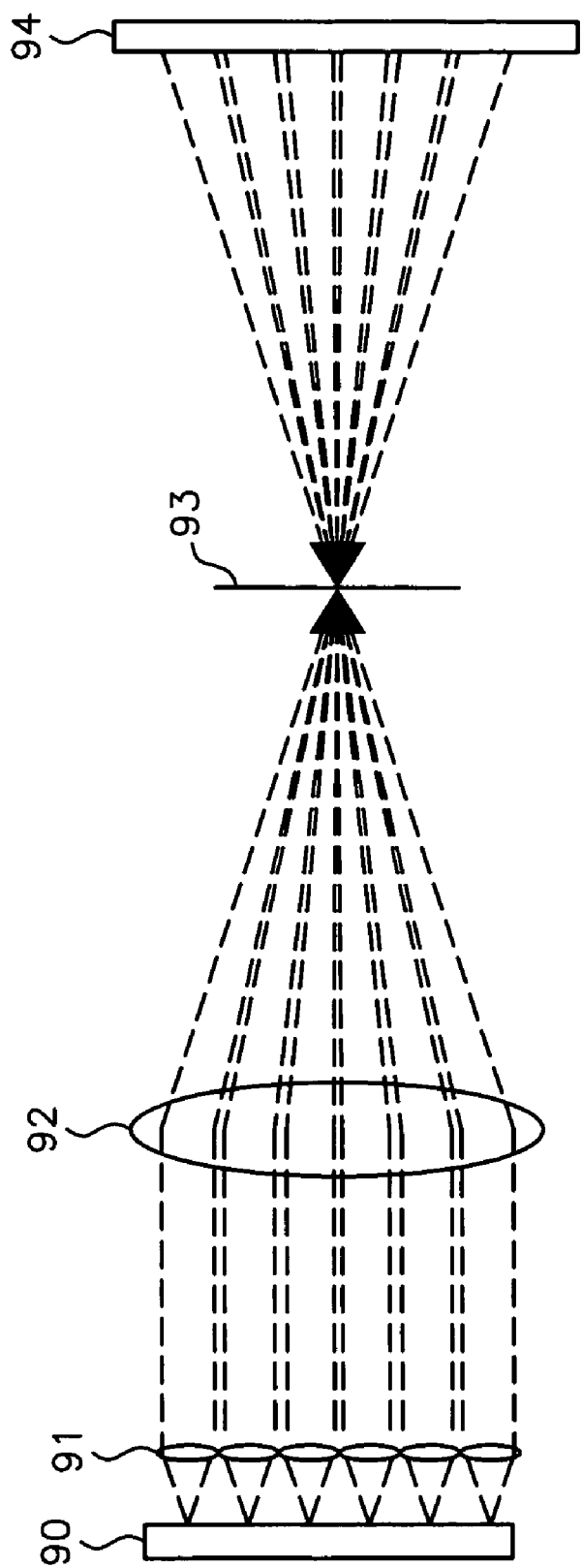
FIG. 9 schematically shows an example illustration of a prior art optical system that can be employed in combination with the present invention for three-dimensional imaging.

Referring now to FIG. 9 an example illustration of a prior art optical system that can be employed in combination with the present invention for three-dimensional imaging with a scanning objective is schematically shown. In one example embodiment, a confocal arrangement with an extended lateral field of view can be obtained using a microlens array, in a similar manner to that described by H J Tiziani and M I Uhde, in their article entitled "Three-dimensional analysis by a microlens array confocal arrangements (*Applied Optics* 33, 567 [1994]). The present invention offers an improvement over their system, in that the axial scanning is continuous, not discrete, within and beyond the specimen volume. In this embodiment, a microlens array 91 scans through the specimen 90 thickness, and a pinhole is located in the back focal plane of a second lens 92, which is located between the pinhole 93 and the microlens array 91. By placing a detector array 94 behind the pinhole 93, an image of the focal plane may be obtained, having good rejection of out-of-focus axial planes and a wide lateral field of view. The field of view so acquired may be larger than that for a conventional confocal arrangement; however, it will be sampled at an interval corresponding to the pitch of the lenses in the microlens array 91. For an N×N array, this arrangement allows the number of scanning points to be reduced by a factor of $N^2$ for the same field of view. As with the other embodiments, projection images are taken from multiple perspectives about an arc of up to 180 degrees.

Point Source-Based Projection Embodiments

Types of Illumination Point Sources

Each source may have the same general characteristics, preferably:

- it may approximate a small circular point source for use in cone beam geometry,
- it may be bright, uniform and with known spectral content,
- the photons emitted from the source may have a known geometry such as a cone beam or a fan beam.

Further, the wavelength of the sources is selectable either by use of various diode emitters or other lasers or by bandpass filtering of a white or other broadband source, for example a mercury or xenon arc lamp.

There are several options that can be employed to create micron-sized or submicron-sized optical point sources, such as:

- a pinhole in front of a laser or other high intensity photon source,
- an optical fiber with a small cross-section and small apparent aperture,
- a short focal length lens in front of a photon source,
- an electron beam that irradiates a point on a phosphor surface (a form of CRT), and
- various combinations of the above.

As used herein, the point sources referred to above are of course not ideal point sources since they must be of a finite size in order to transmit light through an aperture. The finite size of the illumination light source gives rise to an angular error in which even straight line light rays overlap to reduce resolution and contrast in the shadowgram. Reducing the size of this source while maintaining high enough light intensity throughput for the detection system is desired to obtain a high quality shadowgram. Smaller sized apertures can be created using photonics crystal fiber, with its current core size as small as 1 micron, and due to different physical laws governing its means of light transmission, smaller core sizes can be expected in the future. Another recent photonics development, surface-plasmon enhanced transmission, can be employed not only to increase light throughput, but may also be used to control the exit angle of the light from the aperture. Typically these illumination systems use laser light sources, possibly destroying the optical coherence by passing the beam of light through a distribution of optical path differences of up to $+/-\lambda$, in parallel.

Minimization of Source-Object-Detector Distance

Minimizing the source-object-detector distance is critical, since the detector must in the near field (i.e., multiple Fresnel zones), roughly characterized as $R<D^2/\lambda$, where R is the distance from the detector to the scattering plane and D is the desired lateral spatial resolution. Beyond this point, far-field diffraction (Fraunhofer diffraction) predominates.

The geometry is such that, the closer the point source to the object of interest (the cell), the higher the magnification due to the wider geometric angle that is subtended by an object closer to the source. Magnification in a simple point-source projection system is approximately $M=(A+B)/A$, where A is the distance between the point source and the object (cell) and B is the distance between the object and the detector. Conversely, if the required resolution is known in advance of the system design, then the geometry can be optimized for that particular resolution.

Figure 10:
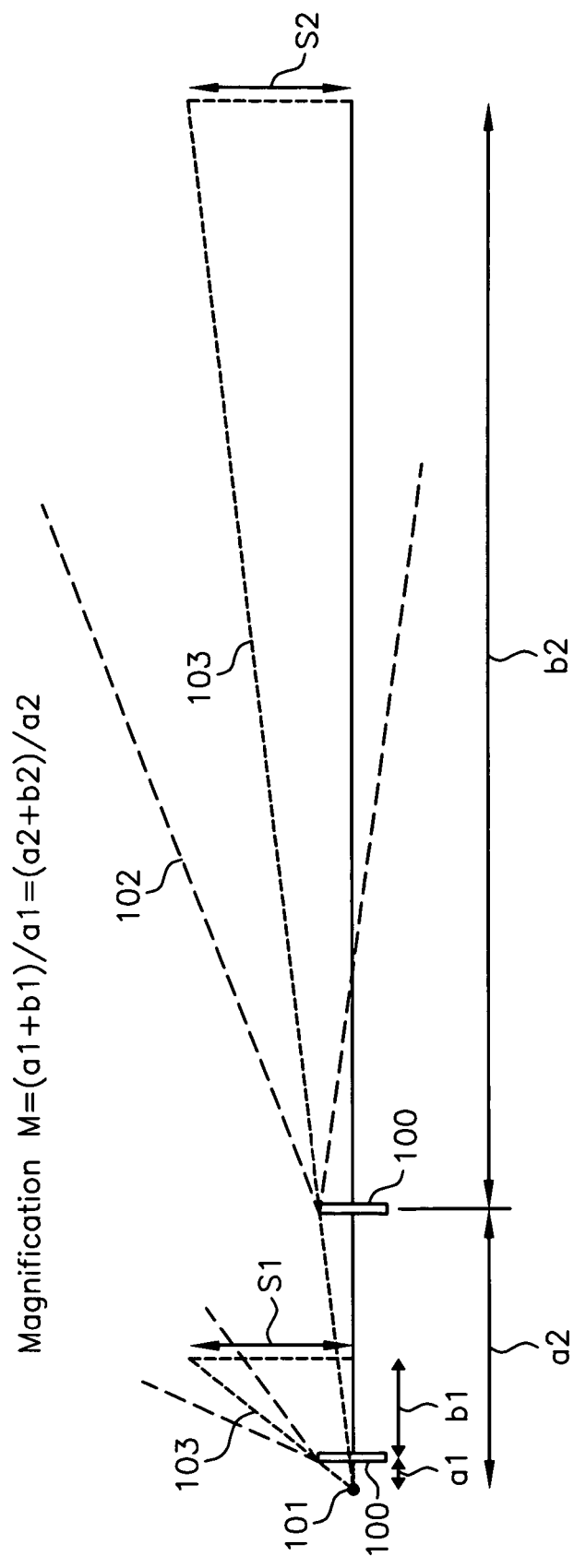
FIG. 10 schematically shows an example of a geometric advantage of minimizing the distances between source and object in accordance with the teachings of the present invention.

FIG. 10 shows the geometric advantage of minimizing the distances between source and object. When the object 100, such as nucleus 2, is placed far away from the illumination source 101 at distance a2, the illumination cone angle is on the order of the scatter angle 102, so by the time desired magnification M is achieved at plane S2, the scattered light completely envelops the area that the straight ray path light 103 covers. However, when the object 100 is placed near the source 101 at distance a1, the detector 12 may be positioned closer, at distance S1, while still achieving the desired magnification, thereby substantially minimizing the spread of the scattered light over an area. Because the illuminating light is now projected through a large exit angle, scattered light tends to separate out and not completely envelop the area covered by the straight ray path light. Note that at plane S1 there is a region in the shadow of the object where scattered light may not affect at all.

Figure 11:
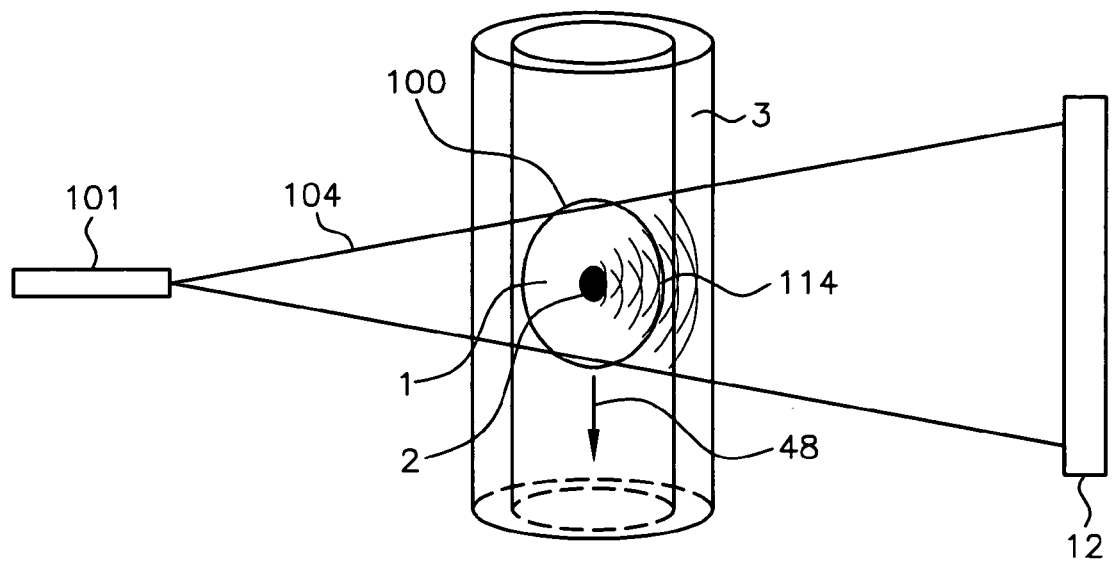
FIG. 11 schematically shows an example of significant diffraction that occurs when light is projected past a light-attenuating region of interest (ROI) around a specimen.

FIG. 11 illustrates the importance of, first, reducing the contribution of scattered light to the formation of a standard shadowgram by insuring that the illumination light cone 104 does not overfill the region of interest (ROI) object 100. In a specific case, this ROI may be the cell nucleus 2. As a result the high intensity light that diffracts 114 around the boundary of the ROI and its surroundings (e.g. the plasma membrane of a cell where the ROI is the nucleus). Thus adding unwanted noise, helping to obscure an ideal shadowgram that is based on absorption.

A second consideration involves close placement of the object ROI 100 to a high exit numerical aperture source so that the overall distance between source, object, and detector is minimized. Such close placement substantially reduces the contribution of non-ballistic light scattered through an off-axis angle because the light has less chance to spread out and obscure the ideal straight ray path shadowgram. Furthermore, the high exit angle of the light of the point source is advantageous because light is mostly scattered through a shallow off-axis angle centered around the incident ray vector, thereby potentially creating more spatial separation between straight ray path light and scattered off-axis light Due to the typical sizes objects within the specimen ROI being on the scale of microns, and the wavelengths of light used for optical tomography being 0.3 to 1 micron, significant diffraction occurs when the light is projected through the light-attenuating ROI and its surroundings. Thus, the light signal detected, ideally being a geometrically determined densitometric image, is greatly obscured by the relatively high intensity of light that diffracts around the ROI, which in the case of cells may be roughly 100 microns in diameter.

Thus, it is advantageous to reduce this diffraction and refraction by minimizing any mismatch of reflective index outside the ROI.

Using Virtual Point Sources

Figure 12:
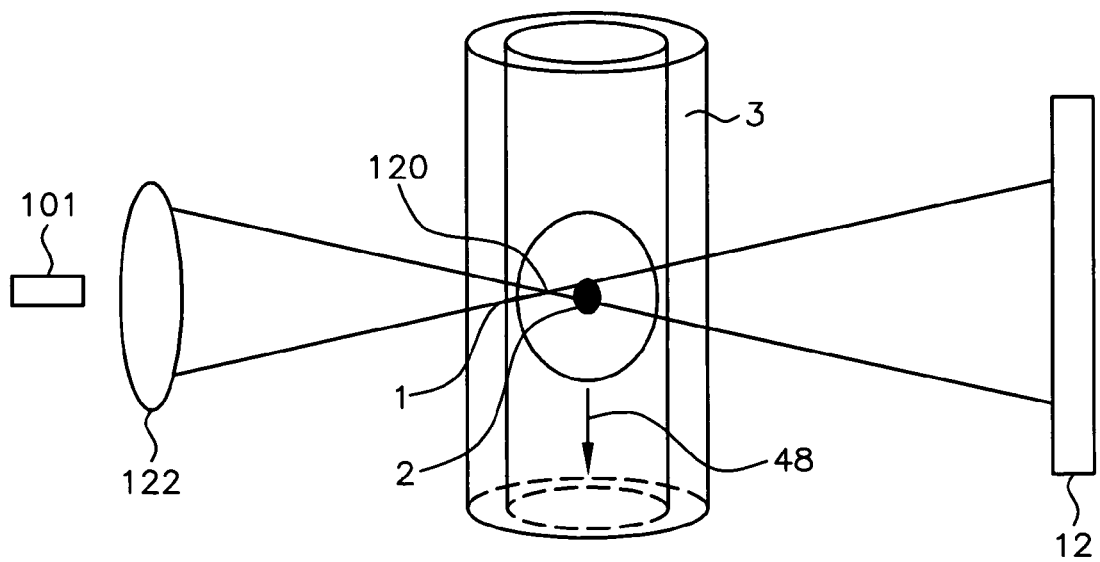
FIG. 12 schematically shows an example of a virtual light source arranged in accordance with the principles of the present invention.

FIG. 12 shows an example of a virtual point source 120 created from projecting a point source 101 through optical component 122. The use of a virtual point source 120 greatly improves the contrast in the transmittance image because light that previously may have diffracted around the ROI into the center of the image, or passed entirely outside the ROI, is more efficiently projected into the ROI. However, this configuration limits the sampling of the ROI to a sub-region within the ROI. In a tomographic reconstruction utilizing multiple perspectives around the ROI, the resultant three-dimensional data set would be a relatively thick slice through the ROI, but with relatively better image quality in the absence of diffraction from the perimeter of the ROI and full utilization of all the photon intensity from the source. This will be particularly useful in quantitative densitometry with stoichiometric stains or labeled molecular probes.

It would be beneficial to locate the point source 101 close to the object ROI 100, but because the object of interest is typically contained within a quartz micro-capillary tube 3 with outside diameter approximately 150 microns. In one example, a light source may advantageously be physically located no closer than 200 to 300 microns from the center of a cell within the flow micro-capillary tube. To overcome such physical constraints, an external set of optical components can be used to focus a virtual point inside the micro-capillary tube, closer to the cell. Virtual light source(s) can be used in an optical tomography system to maintain the requirement of possessing small (sub-micron) source size wherein all of the source photons pass through the ROI. Because the sample is typically an aqueous solution, a solid immersion lens can be used in place of the standard objective lens, with the illumination source embedded in the lens; this provides the higher index of refraction needed to decrease the focal spot size further, as the wavelength and angle of incidence are already at practical limits.

There is a further benefit of the close placement of a virtual point source near the ROI. If coherent light is used, then speckle patterns appear as a result of interference between the coherent diffracted light waves. By eliminating a majority of the diffracted light (around the edge of the ROI) from the transmittance image, a coherent source may be used with minimal speckle noise. Coherent sources include laser diodes and lasers, which are typically the highest energy density sources available, and allow more photons to be pumped into a small area. This allows the reduction of exposure time that may be necessary to obtain the transmittance image that is not motion blurred, (i.e., blurred using pulsed illumination of very short duration) and, in turn, allows higher specimen-throughput rates while potentially substantially improving resolution in the shadowgram.

Referring now jointly to FIG. 11 and FIG. 12 an example of significant diffraction that occurs when light is projected past a light-attenuating region of interest (ROI) around a specimen is schematically shown. A light source 101 illuminates a flow micro-capillary tube 3 containing a specimen such as cell 1 having a region of interest (ROI) 100 and a flow direction 48. The light source 101 produces a projected illumination cone 104 that impinges on the ROI 100 producing diffraction 114 around the edges of the ROI. The projection illumination cone forms a shadowgram image on a two dimensional (2D) detector array 12. In a preferred embodiment, the light source is preferably a point source as understood by one skilled in the art and/or as described, for example in Nelson's U.S. patent application Ser. No. 10/126,026.

Using Cell Membrane-Embedded Probes

Figure 13A:
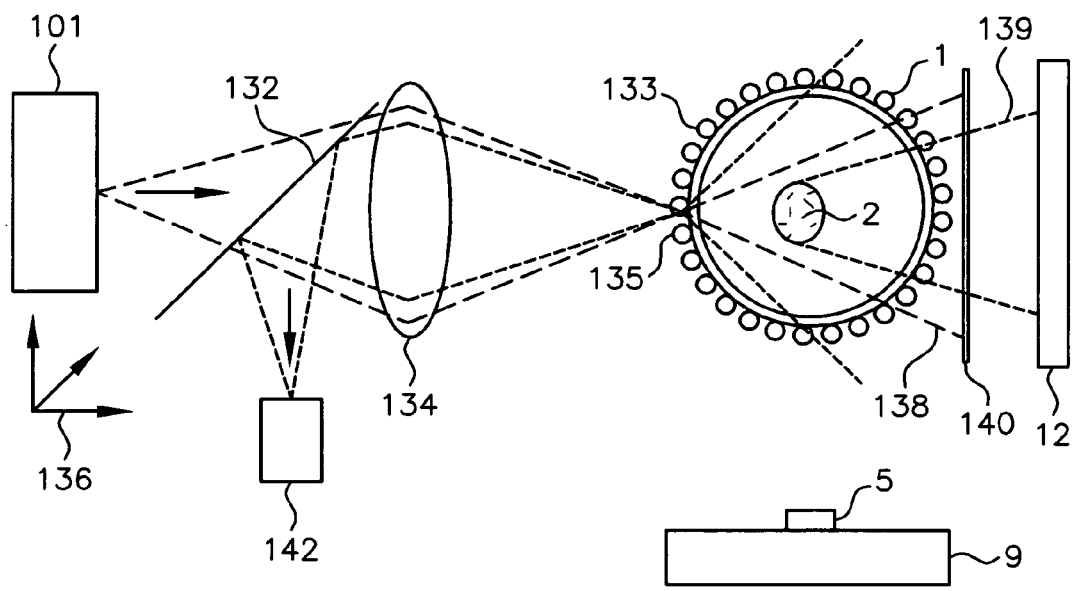
FIG. 13A schematically shows a method for shadowgram formation using wavelength-shifting probes bound to a cell where the probe determines point source dimension.
Figure 13B:
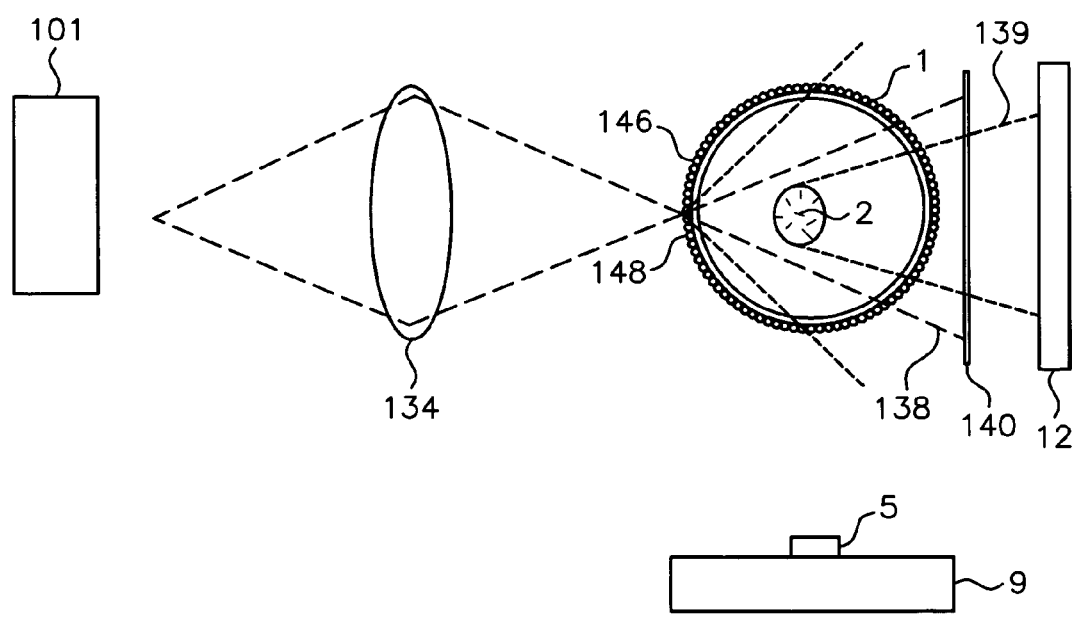
FIG. 13B schematically shows a method for shadowgram formation using wavelength-shifting probes bound to a cell where the probe is smaller than the focal point size.

Now referring to FIGS. 13A and 13B, an alternative method is shown for creating a virtual point source of light adjacent to the cell by employing a secondary micro-sources of light embedded in or bonded to the cell. As discussed earlier, when generating shadowgrams using point sources of illumination where the wavelength of illumination is on the order of the desired resolution in the shadowgram, the source-to-object-to-detector distance should be minimized to obtain the best resolution. By labeling the cell boundary 1 (either the cytoplasmic boundary or the nucleus 2 boundary) with a wavelength-shifting label 133 (e.g. microsphere containing fluorophores or quantum dots), a real illumination point source is placed in very close proximity to the object (that of the cell). FIG. 13A shows a label 135 on the cell boundary is excited by the illumination light, either a standard illumination source such as an arc lamp, a laser, or by a two-photon source. The excitation of the label causes an emission light 139 at a different wavelength, and through use of an optical element 140, such as a bandpass filter or dichroic beamsplitter, the excitation light 138 is blocked from reaching the detector array 12, where the absorption 'image' is formed. Thus a point source is formed by the label 135 in close proximity to the object (here, for example, the nucleus 2), providing the best possible resolution. The advantage of using a fluorescent-shifted wavelength of light as the excitation source for optical tomography is the incoherent nature of the light and the ability to filter the point source from the focused beam of light. Scatter of the emission light can be rejected by limited acceptance angle of the detector, or by confocality as described previously in this section. The advantage of using fluorescent-labeled microspheres is that the fluorescence does not photobleach during excitation because the fluorophores are embedded in a material that prevents contact with oxygen and free radicals.

FIGS. 13A and 13B illustrate the difference between sizes and densities of the wavelength-shifting label. In FIG. 13A, the label density is kept somewhat low, such that only a single label is excited at a time, with the diameter of the label determining the point source dimension. When a sparse density of labels is used, then the sample or focused beam must be moved to align the label with the focused beam. This alignment can be determined to be optimal when the emitted fluorescence light is at a maximum using a photodetector 142 on the same side of the sample as the focused beam of excitation light. A translation stage 9 and rotation stage 5 adjusts the position of the cell, or a translation stage 136 adjusts the position of the light source, causing a shift in the position of excitation.

FIG. 13B is meant to illustrate the possibility of using a much higher density, smaller diameter label 146 (i.e. where label diameter <<excitation beam diameter). In this case the beam diameter determines the dimension of point source 148, and alleviates potential problems of not knowing the exact location of the label. This process of excitation of a label or group of labels and recording of the image incident on the detector array must be repeated a multitude of times at different locations. For optical tomography, the location of the point sources relative to one another must be known and recorded in order for a proper computed reconstruction to be done. Relative position of the series of excitation points around the cell can be determined by measuring the depth of focus and the extent of sample rotation and translations done between each measurement.

In another embodiment, element 140 is a dichroic beamsplitter, such that both emission and excitation light may be measured with two separate detector arrays 12.

By Limiting the Acceptance Angle of the Detector

Figure 14A:
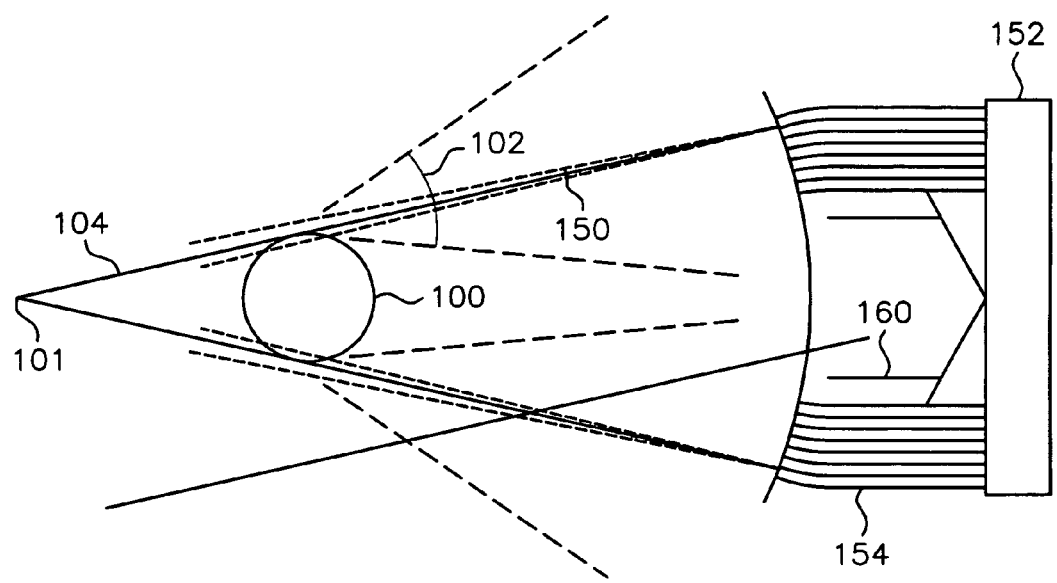
FIG. 14A schematically shows an example of an arrangement of collimators in an array that have a limited acceptance angle so that a large percentage of scattered light is rejected based on angle constructed in accordance with the teachings of the present invention.

Referring now to FIG. 14A, an arrangement of collimators in an array that have a limited acceptance angle so that a large percentage of scattered light is rejected based on angle is schematically shown. One effective method for removing photons that do not conform to the straight line paths originating at an illumination source 101, necessary for tomographic image reconstruction, is to place a collimator 154 with a reduced entrance numerical aperture between an object 100 and a detector 152. Such a device limits the acceptance angle 150 for each pixel in the shadowgram. This acceptance angle should be less than an illumination scatter angle 102. However, the most effective and efficient collimator should eliminate incoming photons with channel size no larger than the single pixels of the detector array. Moreover, it is desirable to avoid "cross talk" between channels so as not to contaminate adjacent pixels.

In the example shown, an illumination source 101, such as listed in the previous section on types of illumination sources, projects a light beam 104 impinging on an object in a region of interest 100. A collimator array 154 including a plurality of collimator fibers wherein each fiber is mapped to a single pixel on a photosensor array 152 as schematically represented by arrow 160. The photosensor array 152 may advantageously comprise a CCD array or equivalent sensor array.

In one embodiment, a collimator may advantageously be mounted against, or in close proximity to, the detector surface wherein the collimator contains channels matched to the detector pixel size. This channel collimator is comprised of glass fibers or tubes that have been bundled and thinned and which may be coated and clad to create a matrix of channel elements that absorb photons with undesired trajectories. Further, the collimator front surface can be shaped so as to create a constant numerical aperture (NA) for a given arrangement of source/object/detector. Typically, this would be achieved by polishing a spherical concave surface into the front surface of the coherent fiberoptic bundle that is attached to the detector. By controlling the length of the collimator, the cladding, the absorbing coating between the fibers, the diameter of each channel and the distance from the object to the detector, the system may be substantially optimized for detector fill factor, contrast, resolution and signal-to-noise. Thus the collimator can be highly effective in increasing the effective MTF of the system for optimal 3D image reconstruction.

Figure 14B:
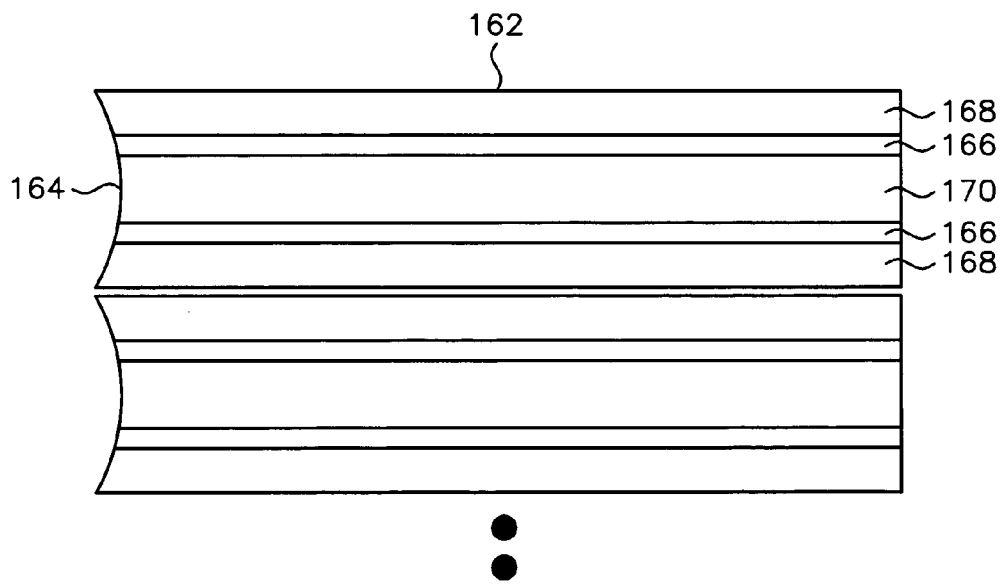
FIG. 14B is a more detailed magnified view of a section of the array of collimators of FIG. 14A.

Referring now to FIG. 14B, a more detailed magnified view of a section of the array of collimators of FIG. 14A is shown. A plurality of collimators 162 each includes an absorbing layer 166, cladding 168 and a core 170. The collimators may include an input end having an optional, slightly concave angle 164. In one example the core diameter may advantageously be on the order of 3 µm where the fibers have a NA of about 0.11. However, with absorbing layer 166 present, core diameter, and length of the fiber will determine the effective NA, with values of NA<<0.11.

Figure 15A:
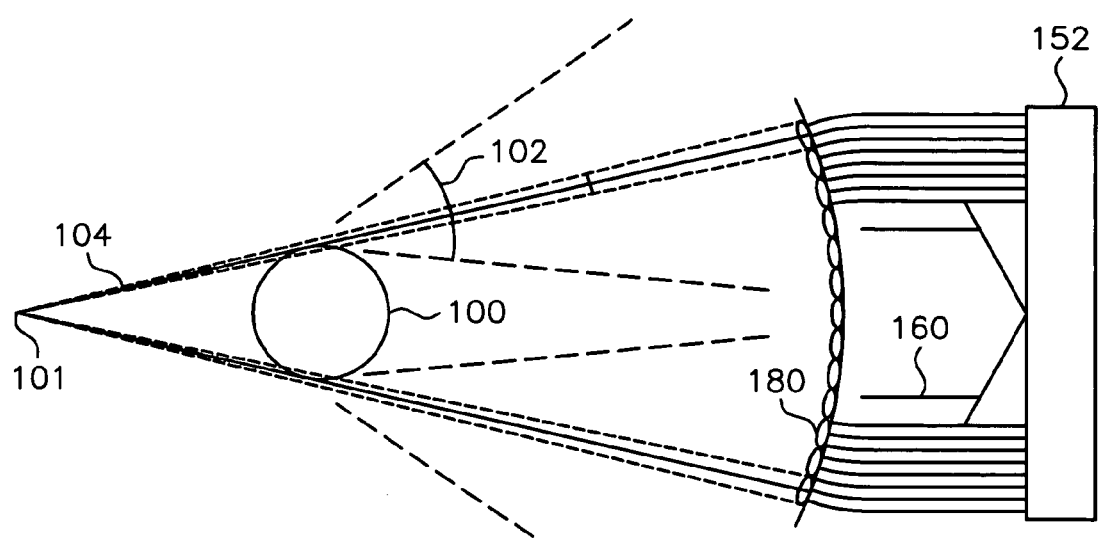
FIG. 15A schematically shows an alternate example of a collimator configuration with a microlens array to further restrict or vary acceptance angle at each detection point constructed in accordance with the teachings of the present invention.

Referring now to FIG. 15A, an alternate example of a collimator configuration with the addition of a microlens array to further restrict acceptance angle at each detection point constructed in accordance with the teachings of the present invention is schematically shown. FIG. 15A shows a collimator configuration similar to FIG. 14A, but with the addition of a microlens array 180 to further restrict or vary acceptance angle at each detection point on the sensor array 152. In yet another example embodiment, a microlens array can be used in front of the fiber array or formed onto the surface of each optical fiber within the coherent fiber bundle to further limit or vary acceptance angle, thereby increasing the rejection of scattered light. The advantage of this microlens addition to each collimator or optical fiber is the ability to use standard components and vary their acceptance NA to match the specific need of the optical tomography instrument.

Figure 15B:
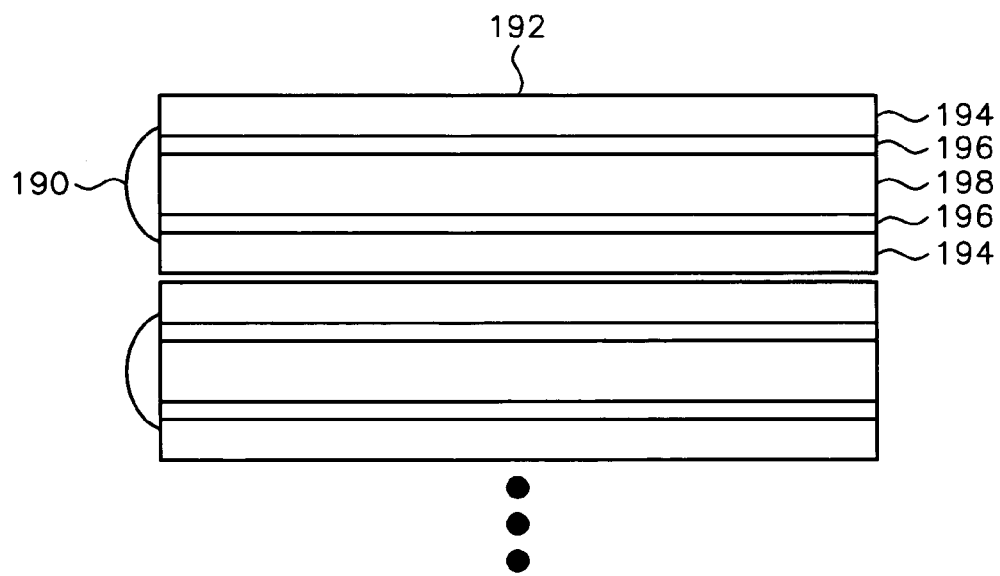
FIG. 15B is a more detailed magnified view of a section of the array of collimators of FIG. 15A.

Referring now to FIG. 15B, a more detailed magnified view of a section of the array of collimators of FIG. 15A is shown. A plurality of collimators 192 each includes an absorbing layer 194, cladding 196 and a core 198. The collimators may include an input end including a micro-lens 190. The difference in index of refraction of core versus cladding can be varied to determine the effective numerical aperture, with wave-guided light that exceeds the associated critical angle subsequently striking the absorbing layer 194 and attenuated. In one example the core diameter may advantageously be on the order of 3 µm where the fibers have a variable NA.

By Polarization

Figure 16:
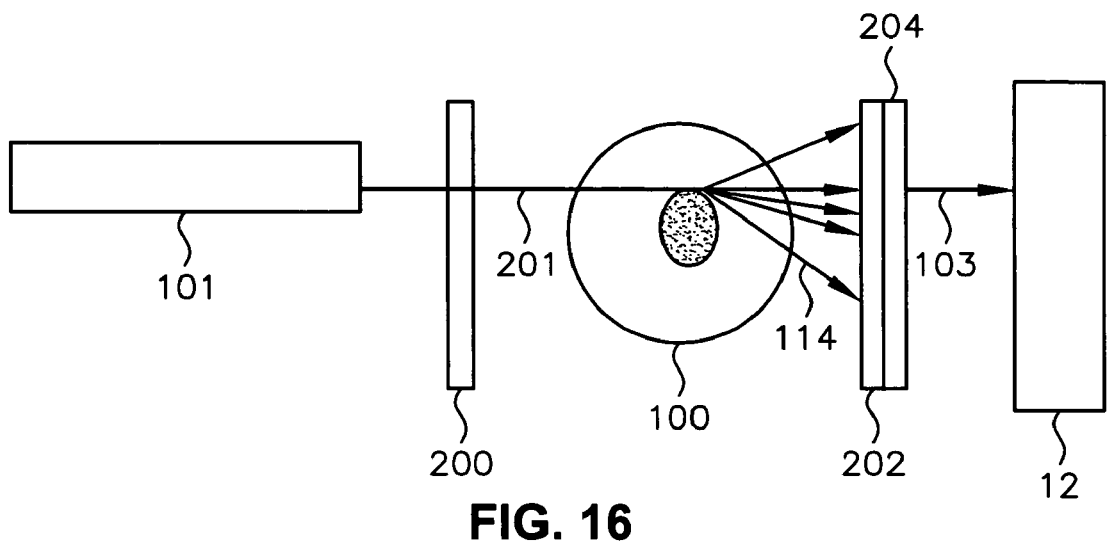
FIG. 16 schematically shows an example illustrating the use of polarization filters and/or phase plates in a three-dimensional image reconstruction as contemplated by an embodiment of the present invention.

Referring now to FIG. 16, there shown schematically is an example illustrating the use of polarization filters (and/or a phase plate) in a three-dimensional (3D) image reconstruction as contemplated by an embodiment of the present invention. All image reconstruction algorithms are vulnerable to various forms of noise in the projection data, such as scatter and diffraction. Light scatter and diffraction may become significant in optical tomography where the wavelength of the illuminating photons is of the same order as the desired resolution within the object to be reconstructed and where the object contains structures that are of the same order in size as the illuminating wavelength. Interactions that can change the polarization of photons or cause a phase shift provide an opportunity to remove or reduce the contamination in a projection image through the use of polarization filters and/or a phase plate. For example, if a point source 101 is filtered through a first linear polarizer 200, then a first polarized light ray 201 is produced that impinges on object 100. Rays 114 represent photons scattered as a result of the first polarized light ray 201 impinging on the object 100. A surface of a sensor 12, positioned to sense a projection image generated by the point source 101, is similarly filtered through a second linear polarizer 202 having the same orientation as the first linear polarizer 200. As indicated by the rays 114, photons whose polarization vector has shifted will be removed from detection. At the same time, unscattered light rays will pass through both polarization filters resulting in a portion of unscattered light 103, impinging on the detector 12. To remove phase shift, a phase plate 204 can be placed proximate the second linear polarizer 202. In this way, the background of noise due to shifts in polarization and phase can be reduced significantly.

By Shorter Ultraviolet Wavelengths

Visible wavelengths (400-700 nm) require the use of a label or dye to visualize cellular structure. However, with ultraviolet wavelengths (10-400 nm), natural absorption occurs in the ultraviolet range, thus processing of the cells to label them may no longer necessary. Differences in absorbance of proteins compared with absorbance of nucleic acids as a function of wavelength may also be used to discern relative contributions of these two distinct cellular components. Because the wavelength is significantly shorter than the desired resolution or minimum feature size of interest, diffraction is less of a problem, and signal-to-noise in the shadowgram is improved.

By Confocal-Like Rejection

Figure 17:
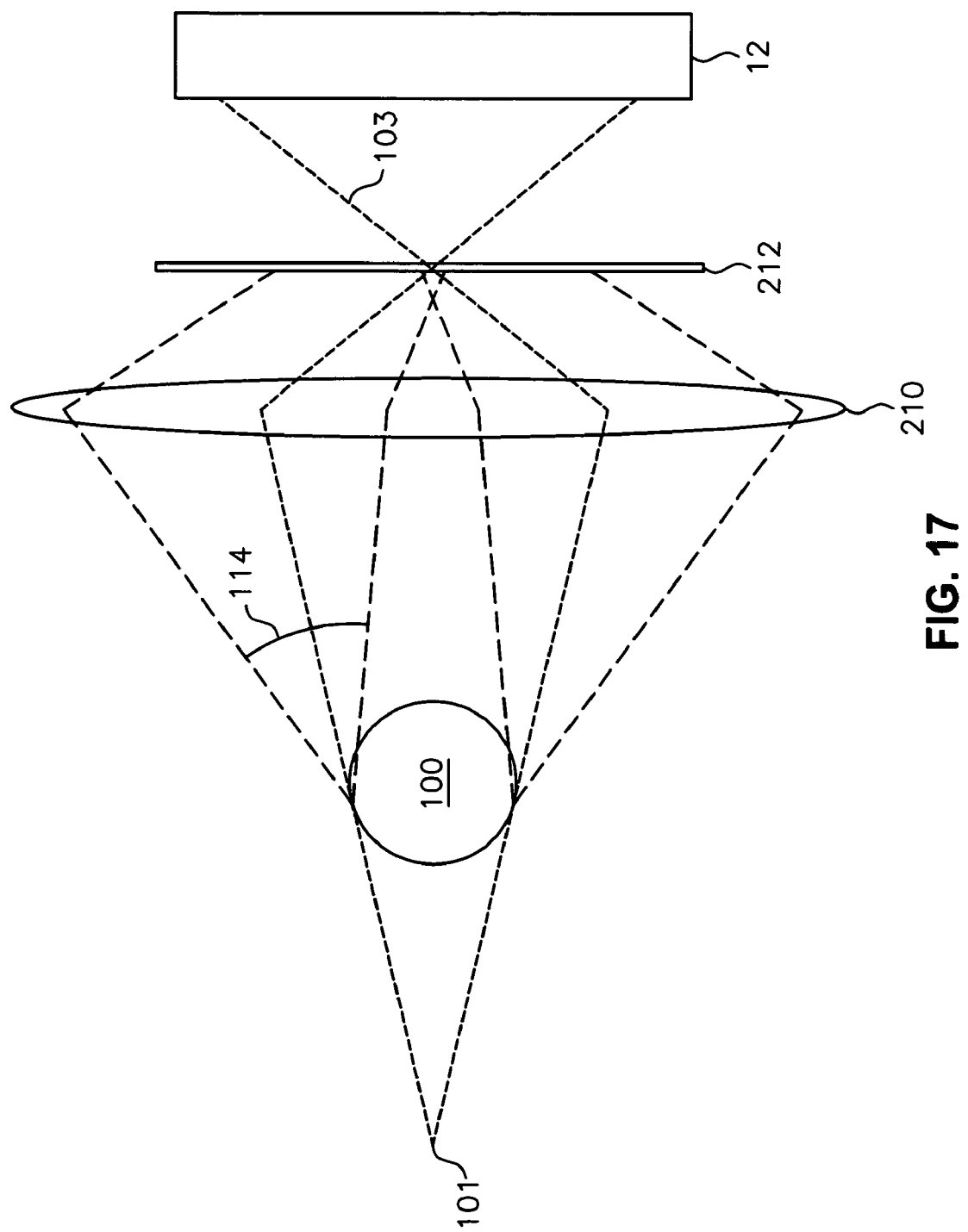
FIG. 17 schematically shows an example of a confocal arrangement that allows rejection of scattered light based on angle, with a pinhole placed at one focal plane to minimize light scattered at the object constructed in accordance with the teachings of the present invention.

Referring now to FIG. 17, by using a lens system 210 combined with a pinhole 212 such that the back focal point of the lens system is placed at the illumination point source 101, scattered light 114 can be rejected from the shadowgram, the shadowgram consisting of straight ray path light 103 incident on detector 12.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, devices and algorithms, and that various modifications, both as to the equipment details and operating procedures, may be accomplished without departing from the true spirit and scope of the present invention.

What is claimed is:

1. A method for multi-dimensional imaging of a specimen region, comprising the steps of:
    a) illuminating the specimen region;
    b) moving an optical element to scan a focal plane through the thickness of the specimen region at a fixed viewpoint to produce a pseudo-projection image of the specimen onto a two-dimensional array of detectors during a single exposure of the two-dimensional array of detectors, wherein the pseudo-projection image thus formed includes an integration of a range of focal plane images; and
    c) repeating steps a) and b) for two or more viewpoints to produce a set of pseudo-projection images.

2. The method of claim 1 wherein steps a) and b) are repeated about an arc at least partially encircling the specimen region.

3. The method of claim 1 wherein steps a) and b) are repeated about multiple arcs with a common line or point of intersection, the multiple arcs at least partially encircling the specimen region.

4. The method of claim 1, further comprising the step of using a computer algorithm to extract features of interest from one or more of the set of pseudo-projection images.

5. The method of claim 1 wherein the optical element comprises an objective lens.

6. The method of claim 1 wherein the step of moving an optical element is accomplished by driving a piezoelectric element coupled to the optical element.

7. The method of claim 1, wherein the specimen region comprises a cell.

8. The method of claim 1, wherein the specimen region comprises an artificially generated test phantom.

9. The method of claim 1 wherein the step of illuminating the specimen region comprises illuminating with a laser.

10. The method of claim 1 wherein the step of illuminating the specimen region comprises illuminating with substantially incoherent light.

11. The method of claim 10 wherein the substantially incoherent light is generated by an arc lamp.

12. The method of claim 1 further comprising interposing at least one microlens array between the specimen region and the two-dimensional array of detectors.

13. The method of claim 1, wherein the optical element is configured in a confocal arrangement with an extended lateral field of view.

14. The method of claim 1, wherein the the step of moving comprises moving an oil-immersion lens along its optical axis.

15. The method of claim 1, wherein the specimen region comprises a specimen within a specimen holder, wherein the specimen holder is selected from the group consisting of a micro-capillary tube, a plastic bead, polymer optical fiber, and a microscope slide.

16. The method of claim 1 further comprising coupling an array of collimator fibers to the two-dimensional array of detectors, wherein each fiber is mapped to a single pixel on the two-dimensional array of detectors.

17. The method of claim 16 wherein the two-dimensional array of detectors comprises a CCD array.

18. The method of claim 1 further comprises positioning a microlens array in front of a fiber bundle, where each fiber is mapped to a region on the two-dimensional array of detectors so as to limit acceptance angle, thereby increasing the rejection of scattered light.

19. The method of claim 1 wherein the two-dimensional array of detectors comprises a coherent fiber bundle attached to a detector pixel array.

20. The method of claim 1, wherein the specimen region comprises a specimen that has been pressure-injected into a micro-capillary tube.

21. A method for multi-dimensional imaging of a specimen region, comprising the steps of:
    a) arranging at least two sets of illumination and image capturing systems in an arc about a specimen region;
    b) operating each set of illumination and image capturing systems to capture images from a continuum of parallel focal planes, where each of the continuum of parallel focal planes is within the specimen region and is substantially perpendicular to the incident light rays from one of said illumination and image capturing systems, such that a set of pseudo-projection images are simultaneously compiled from each of said illumination and image capturing systems, wherein each of the set of pseudo-projection images is produced during a single exposure of one of the illumination and image capturing systems and wherein each of the set of pseudo-projection images includes an integration of a range of focal plane images; and
    c) wherein the arc at least partially encircles the specimen region so that the set of pseudo-projection images is suitable for use in tomographic image reconstruction.

22. The method of claim 1 further including the step of separating at least one of the set of pseudo-projection images based on color to produce two or more images, with one image primarily consisting of features generated by absorption by a dye/marker.

23. The method of claim 1 further comprising the step of separating color in the specimen region to produce two or more pseudo-projection images, with one image primarily consisting of features generated by absorption by a dye/marker.

24. A method for multi-dimensional imaging of a specimen region, comprising:
    a) illuminating the specimen region;
    b) continuously sampling along an optical axis at a fixed viewpoint through the thickness of the specimen region to produce a pseudo-projection image of the specimen onto a two-dimensional array of detectors during a single exposure of the two-dimensional array of detectors, wherein the pseudo-projection image thus formed includes an integration of a range of focal plane images; and
    c) repeating steps a) and b for two or more viewpoints to produce a set of pseudo-projection images.

* * * * *